US009750821B2

(12) United States Patent
Schneider et al.

(10) Patent No.: US 9,750,821 B2
(45) Date of Patent: Sep. 5, 2017

(54) GAS-FILLED MICROVESICLE ASSEMBLY FOR CONTRAST IMAGING

(75) Inventors: Michel Schneider, Troinex (CH); Philippe Bussat, Feigeres (FR); Feng Yan, Grand Lancy (CH); Anne Senente, Carouge (CH)

(73) Assignee: Bracco Suisse S.A., Manno (CH)

( * ) Notice: Subject to any disclaimer, the term of this patent is extended or adjusted under 35 U.S.C. 154(b) by 1634 days.

(21) Appl. No.: 10/584,327

(22) PCT Filed: Dec. 21, 2004

(86) PCT No.: PCT/IB2004/004230
§ 371 (c)(1),
(2), (4) Date: Jun. 21, 2006

(87) PCT Pub. No.: WO2005/063305
PCT Pub. Date: Jul. 14, 2005

(65) Prior Publication Data
US 2007/0071685 A1    Mar. 29, 2007

(30) Foreign Application Priority Data
Dec. 22, 2003  (EP) .................... 03029534

(51) Int. Cl.
*A61K 47/48*  (2006.01)
*A61K 41/00*  (2006.01)
*A61K 49/22*  (2006.01)

(52) U.S. Cl.
CPC .... *A61K 47/48869* (2013.01); *A61K 41/0028* (2013.01); *A61K 49/225* (2013.01)

(58) Field of Classification Search
CPC .............. A61K 41/0028; A61K 49/225; A61K 47/48869
USPC ........................................ 424/9.5, 9.51, 9.52
See application file for complete search history.

(56) References Cited

U.S. PATENT DOCUMENTS

| | | |
|---|---|---|
| 4,276,885 A | 7/1981 | Tickner et al. |
| 4,675,381 A | 6/1987 | Bichon |
| 4,888,398 A | 12/1989 | Bichon et al. |
| 4,892,733 A | 1/1990 | Bichon et al. |
| 5,271,928 A | 12/1993 | Schneider et al. |
| 5,413,774 A | 5/1995 | Schneider et al. |
| 5,445,813 A | 8/1995 | Schneider et al. |
| 5,487,390 A | 1/1996 | Cohen et al. |
| 5,531,980 A | 7/1996 | Schneider et al. |
| 5,545,395 A | 8/1996 | Tournier et al. |
| 5,556,610 A | 9/1996 | Yan et al. |
| 5,562,099 A | 10/1996 | Cohen et al. |
| 5,597,549 A | 1/1997 | Schneider et al. |
| 5,605,673 A | 2/1997 | Schutt et al. |
| 5,626,867 A * | 5/1997 | Eibl et al. ................ 424/450 |
| 5,711,933 A | 1/1998 | Bichon et al. |
| 5,733,572 A | 3/1998 | Unger et al. |
| 5,741,522 A | 4/1998 | Violante et al. |
| 5,827,504 A | 10/1998 | Yan et al. |
| 5,985,247 A | 11/1999 | Soetanto |
| 6,139,818 A | 10/2000 | Bichon et al. |
| 6,139,819 A | 10/2000 | Unger et al. |
| 6,146,657 A | 11/2000 | Unger et al. |
| 6,153,172 A | 11/2000 | Schroder |
| 6,165,442 A | 12/2000 | Swaerd-Nordmo et al. |
| 6,183,725 B1 | 2/2001 | Yan et al. |
| 6,221,337 B1 | 4/2001 | Dugstad et al. |
| 6,245,318 B1 | 6/2001 | Klibanov et al. |
| 6,258,378 B1 | 7/2001 | Schneider et al. |
| 6,280,705 B1 | 8/2001 | Trevino et al. |
| 6,309,665 B2 | 10/2001 | Barthelemy et al. |
| 6,331,289 B1 | 12/2001 | Klaveness et al. |
| 6,333,021 B1 | 12/2001 | Schneider et al. |
| 6,375,931 B2 * | 4/2002 | Østensen et al. ............ 424/9.52 |
| 6,416,740 B1 | 7/2002 | Unger |

(Continued)

FOREIGN PATENT DOCUMENTS

| | | |
|---|---|---|
| EP | 0130935 B1 | 4/1987 |
| EP | 0558748 A1 | 9/1993 |

(Continued)

OTHER PUBLICATIONS

The Free Dictionary, "microemulsion," http://encyclopedia2.thefreedictionary.com/Microemulsion, 2012.*
Katherine C. Grabar et al: "Preparation and Characterization of Au Colloid Monolayers" Analytical Chemistry, vol. 67, No. 4, Feb. 15, 1995, pp. 735-743.
M. Malmsten, "Surfactants and Polymers in Drug Delivery", 2002, Ch. 2, pp. 19-50, Ch. 4, pp. 87-131, Marcel Dekker Inc. Ed.
G.W. Kabalka et al., "Gadolinium-labeled liposomes containing paramagnetic amphipathic agents: targeted MRI contrast agents for the liver", Magnetic Resonance in Medicine, 1988, pp. 89-95, vol. 8, Academic Press, Inc.
Edited by R. R. C. New "Liposomes, a practical approach", 1989, pp. 45-55, Oxford University Press, Oxford, New York, Tokyo.

(Continued)

Primary Examiner — Michael G Hartley
Assistant Examiner — Leah Schlientz
(74) Attorney, Agent, or Firm — Vivicar Law, PLLC

(57) ABSTRACT

Assembly comprising a gas-filled microvesicle and a structural entity which is capable to associate through an electrostatic interaction to the outer surface of said microvesicle (microvesicle associated component—MAC), thereby modifying the physico-chemical properties thereof. Said MAC may optionally comprise a targeting ligand, a bioactive agent, a diagnostic agent or any combination thereof. The assembly of the invention can be formed from gasfilled microbubbles or microballoons and a MAC having a diameter of less than 100 pm, in particular a micelle and is used as an active component in diagnostically and/or therapeutically active formulations, in particular for enhancing the imaging in the field of ultrasound contrast imaging, including targeted ultrasound imaging, ultrasound-mediated drug delivery and other imaging techniques such as molecular resonance imaging (MRI) or nuclear imaging.

32 Claims, 2 Drawing Sheets

(56) References Cited

U.S. PATENT DOCUMENTS

| | | | |
|---|---|---|---|
| 6,576,220 | B2 | 6/2003 | Unger |
| 6,793,626 | B2 | 9/2004 | Tsuzuki |
| 7,083,572 | B2* | 8/2006 | Unger et al. .................. 600/458 |
| 8,460,637 | B2 | 6/2013 | Ottoboni et al. |
| 9,248,204 | B2 | 2/2016 | Bussat et al. |
| 9,364,569 | B2 | 6/2016 | Schneider et al. |
| 2002/0031476 | A1 | 3/2002 | Trevino et al. |
| 2002/0102216 | A1 | 8/2002 | Lanza et al. |
| 2002/0102217 | A1 | 8/2002 | Klaveness et al. |
| 2002/0159952 | A1 | 10/2002 | Unger |
| 2002/0169138 | A1* | 11/2002 | Kunz et al. ....................... 514/44 |
| 2004/0146462 | A1* | 7/2004 | Eriksen et al. ............... 424/9.51 |
| 2005/0130167 | A1* | 6/2005 | Bao et al. .......................... 435/6 |
| 2008/0063603 | A1 | 3/2008 | Schneider et al. |
| 2016/0184464 | A1 | 6/2016 | Bussat et al. |

FOREIGN PATENT DOCUMENTS

| | | |
|---|---|---|
| EP | 0324938 B1 | 11/1993 |
| EP | 0554213 B1 | 1/1997 |
| EP | 1073473 B1 | 7/2001 |
| EP | 1228770 A1 | 8/2002 |
| EP | 0804251 B1 | 9/2002 |
| EP | 1419789 A2 | 5/2004 |
| EP | 1228770 81 | 7/2005 |
| JP | 07-503976 T | 4/1995 |
| JP | 2000143550 * | 5/2000 ............ A61K 49/00 |
| JP | 2001-508454 A | 6/2001 |
| JP | 2001511765 A | 8/2001 |
| JP | 2001-524983 A | 12/2001 |
| JP | 2002-502829 A | 1/2002 |
| JP | 2002-512206 A | 4/2002 |
| JP | 2002-212108 A | 7/2002 |
| JP | 2002-522379 A | 7/2002 |
| JP | 2007-515470 A | 6/2007 |
| JP | 2007515471 | 6/2007 |
| WO | WO 87/03891 | 7/1987 |
| WO | WO 91/15244 A2 | 10/1991 |
| WO | 92-09829 A1 | 6/1992 |
| WO | 94-01140 A1 | 1/1994 |
| WO | 94/04197 A1 | 3/1994 |
| WO | WO 94/09829 A1 | 5/1994 |
| WO | WO 94/28873 A1 | 12/1994 |
| WO | WO 95/23615 A1 | 9/1995 |
| WO | 96-07434 A1 | 3/1996 |
| WO | 96-09037 A1 | 3/1996 |
| WO | 97-29782 A1 | 8/1997 |
| WO | WO 97/29783 A1 | 8/1997 |
| WO | 97-40858 A1 | 11/1997 |
| WO | 98-04074 A1 | 1/1998 |
| WO | 98-05364 A2 | 2/1998 |
| WO | 98/18500 A2 | 5/1998 |
| WO | WO 98/18501 A2 | 5/1998 |
| WO | 98-32468 A1 | 7/1998 |
| WO | 98-42383 A1 | 10/1998 |
| WO | 98-42384 A1 | 10/1998 |
| WO | 98/51284 A1 | 11/1998 |
| WO | 99-08716 A2 | 2/1999 |
| WO | 99-20312 A1 | 4/1999 |
| WO | 99-36104 A2 | 7/1999 |
| WO | 99/39738 A1 | 8/1999 |
| WO | WO 99/39738 A1 | 8/1999 |
| WO | WO 99/53963 A1 | 10/1999 |
| WO | WO 99/55383 A2 | 11/1999 |
| WO | 01/68150 A1 | 9/2001 |
| WO | WO 02/055544 A2 | 7/2002 |
| WO | WO 03/005029 * | 1/2003 .......... B01N 33/543 |
| WO | WO 03/015831 A1 | 2/2003 |
| WO | WO 03/074005 A2 | 9/2003 |
| WO | WO 03/084574 A1 | 10/2003 |
| WO | 04-001140 A1 | 12/2003 |
| WO | WO 2004/069284 A2 | 8/2004 |
| WO | WO 2004/069284 A3 | 8/2004 |
| WO | 2005-063305 A1 | 7/2005 |
| WO | 2005/063306 A1 | 7/2005 |
| WO | 2005-070472 A2 | 8/2005 |

OTHER PUBLICATIONS

PCT Search Report for PCT/IB2004/004230, dated May 30, 2005.
PCT Written Opinion of the ISA, dated May 30, 2005.
PCT International Preliminary Report on Patentability, dated Jul. 6, 2006.
De Jong, N. et al: "Absorption and scatter of encapsulated gas filled microspheres: theoretical considerations and some measurements", Ultrasonics, XP-00267462, Mar. 1992, pp. 95-103, vol. 30, No. 2, Butterworth-Heinemann Ltd., Guildford, Surrey, Great Britain.
Eatock, Brian C., et al., "Numerical studies of the spectrum of low-intensity ultrasound scattered by bubbles" J. Acoust. Soc. Am., vol. 77, No. 5, pp. 1692-1701.
Goertz, D.E. et al., "Effect of Bubble Size Distribution on Nonlinear Scattering from Microbubbles at High Frequencies", IEEE Ultrasonics Symposium Poster Session, 2003, p. 229.
Goertz, D.E. et al., "The Effect of Bubble Size on Nonlinear Scattering From Microbubbles at High Frequencies", IEEE Ultrasonics Symposium, pp. 1503-1506.
Gorce et al., "Influence of Bubble Size Distribution on the Echogenicity of Ultrasound Contrast Agents A Study of SonoVue", Investigative Radiology, Nov. 2000, vol. 35 (11), pp. 661-671, Lippincott Williams Wilkinson, Inc., XP009041823.
Halpern, Ethan J. et al., "Directed Biopsy During Contrast-Enhanced Sonography of the Prostate", AJR, 2002, vol. 178, pp. 915-919.
Hasik, Matthew J. et al., "Evaluation of synthetic phospholipids ultrasound contrast agents", Ultrasonics, 2002, pp. 973-982, Elsevier Science B.V., New York, N.Y.
Kim, Tae-Hwan et al: "One more robust estimation of skewness and kurtosis : simulation and application to the S&P500 Index", Department of Economics, USCD, 2003, US.
Kullberg, Erika Bohl et al., "Development of EGF-Conjugated Liposomes for Targeted Delivery of Boronated DNA-Binding Agents" Bioconjugate Chem., 2002, vol. 13, No. 4, pp. 737-743.
Lockyer, Simon et al., "Demonstration of Flow and Platelet Dependency in a Ferric Chloride-Induced Model of Thrombosis", Journal of Cardiovascular Pharmacology, 1999, vol. 33, No. 5, pp. 718-725.
MacPinsten, Martin, "Surfactants and Polymers in Drug Delivery" Marcel Dekker, pp. 56-60.
Morgan et al: "Experimental and Theoretical Evaluation of Microbubble Behavior: Effect of Transmitted phase and Bubble Size" IEEE Transactions on Ultrasonics, Ferroelectric, and Frequency Control, Nov. 2000, pp. 1494-1509, vol. 47, No. 6.
Ozer, Yekta et al., "Influence of Freezing and Freeze-Drying on the Stability of Liposomes Dispersed in Aqueous Media", Acta Pharm. Technol., 1988, pp. 129-139, vol. 34, No. 3, pp. 129-139.
Patel et al., "Optical and Acoustical Interrogation of Submicron Contrast Agents", IEEE Transactions on Ultrasonics, Ferroelectrics and Frequency Control, 2002, vol. 49, No. 2, pp. 1641-1651.
Scabia et al: "Hardware and software platform for processing and visualization of echographic radio-frequency signals" IEEE Transactions on Ultrasonics, Ferroelectric, and Frequency Control, Oct. 2002, pp. 1444-1452, vol. 49, No. 10.
Schneider,Michel et al., "BR1: a New Ultraonographic Contrast Agent Based on Sulfur Hexafluoride-Filled Microbubbles", Investigative Radiology, 1995, vol. 30, No. 8, pp. 451-457, XP611270.
Office Action for Australian application No. 2005273865, dated Feb. 5, 2010.
Office Action (First) for Chinese application No. 200580028052.9, dated May 8, 2009 (English translation).
Office Action (Second) for Chinese application No. 200580028052.9, dated Mar. 12, 2010 (English translation).
Notification of Re-examination for Chinese application No. 200580028052.9, dated Mar. 20, 2012 (English translation).
Office Action for Japanese application No. 2007-526459, dated Feb. 8, 2011 (English translation).
European Search Report for EP04019557.0, dated Jan. 7, 2005.

(56) References Cited

OTHER PUBLICATIONS

PCT International Search Report for PCT/IB2004/000243, dated Sep. 22, 2004.
PCT Written Opinion for PCT/IB2004/000243, dated Sep. 22, 2004.
PCT International Preliminary Report on Patentability for PCT/IB2004/000243, dated Aug. 5, 2005.
PCT International Search Report for PCT/EP2005/054041, dated Oct. 28, 2005.
PCT Written Opinion for PCT/EP2005/054041, dated Oct. 28, 2005.
Office Action for U.S. Appl. No. 10/544,123, dated Apr. 28, 2009.
Office Action for U.S. Appl. No. 10/544,123, dated Jan. 14, 2014.
PCT Search Report for PCT/IB2004/004233, dated May 30, 2005.
PCT Written Opinion of the ISA for PCT/IB2004/004233, dated May 30, 2005.
PCT International Preliminary Report on Patentability for PCT/IB2004/004233, dated Jul. 6, 2006.
Office Action for Japanese application No. 2011-237685, dated Aug. 6, 2013 (English translation of Office Action summary).
Office Action for Chinese application No. 201310032548.X, dated Dec. 22, 2014 (English translation).
Uster, et al., "Insertion of poly(ethylene glycol) derivatized phospholipid into pre-formed liposomes results in prolonged in vivo circulation time," FEBS Letters, 386:243-246 (1996).
Notice of Allowance for U.S. Appl. No. 11/660,188, dated Aug. 25, 2015.
Office Action for U.S. Appl. No. 11/660,188, dated Dec. 10, 2014.
Office Action for U.S. Appl. No. 11/660,188, dated Jun. 4, 2014.
Office Action for U.S. Appl. No. 11/660,188, dated Nov. 15, 2013.
Office Action for U.S. Appl. No. 11/660,188, dated May 17, 2013.
Office Action for U.S. Appl. No. 11/660,188, dated Sep. 13, 2012.
Office Action for U.S. Appl. No. 11/660,188, dated Jul. 7, 2011.
Office Action for U.S. Appl. No. 11/660,188, dated Dec. 6, 2010.
Office Action for Chinese application No. 201310032548.X, dated Feb. 17, 2014 (English translation).
Notice of Allowance for U.S. Appl. No. 11/660,188, dated Dec. 15, 2015.
Goertz, D.E. et al., "Attenuation and Size Distribution Measurements of Definity and Manipulated Definity Populations", Ultrasound in Med. & Biol., 2007, pp. 1376-1388.
Office Action for U.S. Appl. No. 11/660,188, dated Apr. 4, 2017.

* cited by examiner

GAS-FILLED MICROVESICLE ASSEMBLY FOR CONTRAST IMAGING

This application is the national stage application of corresponding international application number PCT/IB2004/004230 filed Dec. 21, 2004, which claims priority to and the benefit of the European application no. 03029534.9, filed Dec. 22, 2003, all of which are hereby incorporated by reference.

The present invention relates to an assembly comprising as a first component a gas-filled microvesicle and as a second component a structural entity which is capable to associate to the outer surface of the microvesicle, thereby modifying the physico-chemical properties thereof. Optionally, said second component may comprise a targeting ligand, a bioactive agent, a diagnostic agent or any combination thereof. The invention further relates to formulations comprising said assembly, to the use of said formulations, to a method for preparing said assembly and formulations and to a diagnostic kit comprising said assembly. The assembly of the invention can be used as an active component in diagnostically and/or therapeutically active formulations, in particular for enhancing the imaging in the field of ultrasound contrast imaging, including targeted ultrasound imaging and/or ultrasound-mediated drug delivery and other imaging techniques such as molecular resonance imaging (MRI) or nuclear imaging.

BACKGROUND OF THE INVENTION

Rapid development of ultrasound contrast agents in the recent years has generated a number of different formulations, which are useful in ultrasound imaging of organs and tissue of human or animal body. These agents are designed to be used primarily as intravenous or intra-arterial injectables in conjunction with the use of medical echographic equipment which employs for example, B-mode image formation (based on the spatial distribution of backscatter tissue properties) or Doppler signal processing (based on Continuous Wave or pulsed Doppler processing of ultrasonic echoes to determine blood or liquid flow parameters).

A class of injectable formulations useful as ultrasound contrast agents includes suspensions of gas bubbles having a diameter of few microns dispersed in an aqueous medium.

Use of suspensions of gas bubbles in carrier liquid, as efficient ultrasound reflectors is well known in the art. The development of microbubble suspensions as echopharmaceuticals for enhancement of ultrasound imaging followed early observations that rapid intravenous injections of aqueous solutions can cause dissolved gases to come out of solution by forming bubbles. Due to their substantial difference in acoustic impedance relative to blood, these intravascular gas bubbles were found to be excellent reflectors of ultrasound. The injection of suspensions of gas bubbles in a carrier liquid into the blood stream of a living organism strongly reinforces ultrasonic echography imaging, thus enhancing the visualisation of internal organs. Since imaging of organs and deep seated tissues can be crucial in establishing medical diagnosis, a lot of effort has been devoted to the development of stable suspensions of highly concentrated gas bubbles which at the same time would be simple to prepare and administer, would contain a minimum of inactive species and would be capable of long storage and simple administration.

The simple dispersion of free gas bubbles in the aqueous medium is however of limited practical interest, since these bubbles are in general not stable enough to be useful as ultrasound contrast agents.

Interest has accordingly been shown in methods of stabilising gas bubbles for echography and other ultrasonic studies, for example using emulsifiers, oils, thickeners or sugars, or by entrapping or encapsulating the gas or a precursor thereof in a variety of systems. These stabilized gas bubbles are generally referred to in the art as "microvesicles", and may be divided into two main categories.

A first category of stabilized bubbles or microvesicles is generally referred to in the art as "microbubbles" and includes aqueous suspensions in which the bubbles of gas are bounded at the gas/liquid interface by a very thin envelope (film) involving a stabilizing amphiphilic material disposed at the gas to liquid interface. Microbubbles suspensions are typically prepared by contacting powdered amphiphilic materials, e.g. freeze-dried preformed liposomes or freeze-dried or spray-dried phospholipid solutions, with air or other gas and then with an aqueous carrier, while agitating to generate a microbubble suspension which can then be administered, preferably shortly after its preparation.

Examples of aqueous suspension of gas microbubbles and preparation thereof are disclosed, for instance, in U.S. Pat. Nos. 5,271,928, 5,445,813, 5,413,774, 5,556,610, 5,597,549, 5,827,504 and WO 04/069284, which are here incorporated by reference in their entirety.

A second category of microvesicles is generally referred to in the art as "microballoons" or "microcapsules" and includes suspensions in which the bubbles of gas are surrounded by a solid material envelope of a lipid or of natural or synthetic polymers. Examples of microballoons and of the preparation thereof are disclosed, for instance, in U.S. Pat. Nos. 5,711,933 and 6,333,021, herein incorporated by reference in their entirety.

Microvesicles bearing an overall net charges are also known (see for instance International patent application WO 97/29783, herein incorporated by reference); the outer envelope of these microvesicles contains ionic compounds which are capable to confer the desired overall charge to the final microvesicle.

Further to these formulations of gas-filled microvesicles, interest has more recently been shown also towards modified formulations of gas-filled microvesicles, either for improving the diagnostic effect and/or for therapeutic purposes.

For instance, the microvesicles can be associated (e.g. by inclusion in its boundary envelope) with specific components (known as "targeting ligands") which are capable to link to a determined target within a patient's body, e.g. to a specific pathogenic site. These formulations are generally known in the art as "targeted microvesicles". Examples of targeted microvesicles, of targeting ligands and of the preparation thereof are disclosed for instance in International patent application WO 98/18051.

Another example of modified formulations are those where a therapeutic agent is associated with the microvesicle. When the formulation comprising the microvesicle reaches the pathogenic site, the drug can be advantageously released, e.g. by applying a controlled acoustic energy capable of disrupting the vesicle, thus locally releasing the therapeutic agent. This technique is generally known in the field as "ultrasound-mediated drug release". Examples of microvesicles' formulations comprising a therapeutic agent are disclosed for instance in International patent application WO 94/28873.

Further developments in the field have brought to the preparation of assemblies wherein the microvesicle is associated with a second component, bearing a desired therapeutic agent or targeting compound.

For instance, WO 99/39738, discloses an assembly comprising a gas-filled microvesicle and a liquid-filled liposome associated therewith, where the liposome comprises a therapeutically active substance therein. The liposome is associated to the microvesicle by simple admixture with microvesicles or through a link between a conjugated pair, each of the microvesicle and liposome being provided with a component bearing one of the two the respective complementary moieties of said pair (e.g. biotin and avidin or streptavidin).

WO 03/015831 discloses a formulation comprising gas-filled microvesicles ("microspheres" in the application) associated to liposomes, referred to as microsphere-liposome composites. The liposomes of the composite may include a drug and/or a targeting moiety. The microvesicles and liposomes forming the composite are made from a same starting material; the composite is obtained preparing an aqueous solution comprising a mixture of lipids, introducing said solution in a sealed vial comprising the desired gas and finally agitating the solution. The so obtained composite is thus a simple mixture of microvesicles and liposomes of the same chemical nature. In particular, no specific chemical or physical interaction between microvesicles and liposomes is disclosed in said document.

Furthermore, International patent application WO 99/53963 discloses a combined preparation which comprises a first composition comprising gas-filled microvesicles dispersed in an aqueous medium and stabilized by a material and a second composition which is an oil-in-water emulsion comprising a material which stabilize the emulsion. The surface materials stabilizing the microvesicles and the dispersed oil phase have affinity for each other. In one embodiment, said affinity is obtained by using surface materials with opposite charges, so that they interact and bind electrostatically to each other. Alternatively, the association of the respective surface materials may comprises compounds capable of interaction through chemical or biological binding. The oil of the emulsion is a substance which is capable of generating a gas or vapor pressure in vivo and is referred to as the "diffusable component". The association of droplets of said emulsified substance with the microvesicle is capable of determining a controllable growth of the dispersed gas phase in the microvesicle, through inward diffusion thereto of molecules of gas or vapour from said substance.

SUMMARY OF THE INVENTION

The Applicant has now found a novel assembly, for use in pharmaceutically active formulations, comprising a gas-filled microvesicle which is associated to a second component through a substantially electrostatic interaction, said second component optionally comprising a targeting ligand, a bioactive agent, a diagnostic agent or any combination thereof.

An aspect of the present invention relates to an assembly comprising a gas-filled microvesicle bearing a first overall net charge and a component associated to said microvesicle wherein said component bears a second overall net charge opposite in sign to said first net charge, said associated component comprising a biocompatible surface active agent and having a diameter of 100 nm or lower.

According to a preferred embodiment, said associated component comprises a targeting ligand, a bioactive agent, a diagnostic agent or any combination thereof.

Preferably, said surface active agent is an emulsifying agent, a dispersing agent or any combination thereof, particularly preferred being an amphiphilic material.

In the following of this specification, the second component of the assembly will be referred to as Microvesicle's Associated Component ("MAC").

According to an embodiment of the invention, said ultrasound contrast agent is in the form of a suspension of a plurality of said assemblies dispersed in a pharmaceutically acceptable aqueous carrier.

According to an alternative embodiment of the invention said ultrasound contrast agent is in the form of a freeze-dried composition.

Another aspect of the invention relates to a method for preparing an assembly as above described, which comprises admixing a preparation comprising gas-filled microvesicles or a precursor thereof with a preparation comprising said second component or a precursor thereof.

For the purposes of the present application the term "precursor of a gas-filled microvesicles" includes within its meaning any intermediate substance, composition, formulation or structure which is capable of forming a suspension of gas-filled microvesicles including, for instance, freeze-dried formulations capable of being reconstituted with an aqueous carrier to form said microvesicle suspension, or microemulsions capable to undergo a freeze-drying process to obtain a freeze-dried product which can then be reconstituted with an aqueous carrier to form said suspension.

Similarly, the term "precursor of the second component", includes any intermediate substance, composition, formulation or structure which is capable of forming said second component, including, for instance, freeze-dried compositions reconstitutable into an aqueous suspension comprising said MAC.

According to an embodiment of the present invention, the assembly of the invention can be obtained by:

1) preparing a first aqueous suspension comprising a gas-filled microvesicle;
2) preparing a second aqueous suspension comprising a component to be associated with said gas-filled microvesicle;
3) admixing said two suspensions, to obtain an aqueous suspension comprising said assembly.

Optionally a washing step can be included, after the preparation of either the first and/or the second suspension. An optional washing step of the final suspension can also be performed. The term "washing step" includes within its meaning any method or process directed to separate and/or at least partially remove the excess of non-associated materials, components, particles and the like from a suspension of a desired compound (e.g. microvesicle, MAC or assembly). Suitable separation methods include, for instance, decantation, centrifugation, ultrafiltration or microfiltration.

According to an alternative embodiment, the assembly of the invention can be obtained by:

1) preparing a first aqueous suspension comprising a gas-filled microvesicle;
2) freeze-drying said suspension, to obtain a first lyophilized product;
3) preparing a second suspension comprising a component to be associated with said gas-filled microvesicle;
4) freeze-drying said suspension, to obtain a second lyophilized product;

5) reconstituting said first and said second lyophilized product with a physiologically acceptable aqueous carrier in the presence of a gas, to obtain an aqueous suspension comprising the assembly.

Optionally a washing step can be included, after the preparation of either the first and/or the second suspension. An optional washing step of the final suspension can also be performed.

According to a preferred embodiment, the last step 5) of the preparation process comprises the steps of a) reconstituting the second lyophilized product with a physiologically acceptable aqueous carrier to obtain a suspension comprising the component to be associated to the gas-filled microvesicle and b) reconstituting the first lyophilized product with said suspension in the presence of a gas.

According to a further preferred embodiment, said assembly is obtained as a freeze-dried composition by:

1) preparing an aqueous emulsion comprising a water immiscible organic solvent, a phospholipid and a lyoprotecting agent;
2) preparing an aqueous suspension comprising a component to be associated with a gas-filled microvesicle;
3) admixing said aqueous suspension with said aqueous emulsion; and
4) freeze drying the mixture to remove the water and the organic solvent, to obtain a lyophilized product comprising said assembly.

The obtained lyophilized product can be reconstituted into an aqueous suspension comprising an assembly of the invention by agitating said lyophilized product in the presence of a gas and of an aqueous carrier.

A further aspect of the invention relates to a method for ultrasound diagnostic imaging comprising administering a contrast-enhancing amount of an aqueous suspension of an assembly as above defined, optionally comprising a targeting ligand.

A further aspect of the invention relates to a therapeutic method comprising administering a therapeutically-effective amount of an aqueous suspension of an assembly as above defined comprising a bioactive agent.

A still further aspect of the invention relates to a pharmaceutical kit which contains the components of said assembly in any of the following forms: a) as two separate suspensions of microvesicles and MACs; b) as separate freeze-dried preparations of the two components, optionally together with an aqueous carrier for reconstitution; or c) as a freeze-dried preparation of the assembly, together with an aqueous carrier for reconstitution.

An advantage of an assembly according to the invention is that the electrostatic interaction between the microvesicle and the MAC can be obtained by using conventional components typically employed for forming the envelope of the microvesicles, without the need of introducing additional components or moieties in said envelope, which may otherwise impair the stability of the microvesicles.

The obtained assembly can advantageously modify or modulate the behavior of gas-filled microvesicles once administered in the body of a patient (such as, for instance, the rate of clearance from bloodstream circulation). For instance, assemblies comprising positively charged microvesicles and negatively charged MACs can be used to administer a preparation of positively charged microvesicle which will however show a behavior similar to negatively charged microvesicles once inside the body. Alternatively, assemblies comprising negatively charged microvesicles and positively charged MACs can be used to administer a preparation of negatively charged microvesicles which will however show a behavior similar to positively charged microvesicles once inside the body. In addition it is possible to associate a desired targeting compound or a pharmaceutically active agent to the microvesicle without impairing its stability (in particular the stability of the boundary layer surrounding the gas), as said targeting compound or pharmaceutically active agent are in fact associated to the second component of the assembly, which stability is substantially unaffected by the presence of said compound or agent A further advantage of the present invention is the extreme flexibility in the preparation of different assemblies for different purposes. As a matter of fact, a single basic preparation of charged microvesicles can be associated to different preparations of MACs of opposite charge, if necessary more than one at the same time, depending on the specific diagnostic/therapeutic needs. For instance, it is possible to associate to the microvesicles' preparation a first preparation of MAC bearing a targeting ligand (e.g. for binding the assembly to a specific pathogenic site) and a second preparation of MAC including a bioactive agent (which can be released at the specific pathogenic site once the assembly has been linked thereto).

In addition, the Applicant has observed that an assembly of the invention may show an increased pressure resistance with respect to the sole microvesicle.

FIGURES

DETAILED DESCRIPTION OF THE INVENTION

Figure 1:
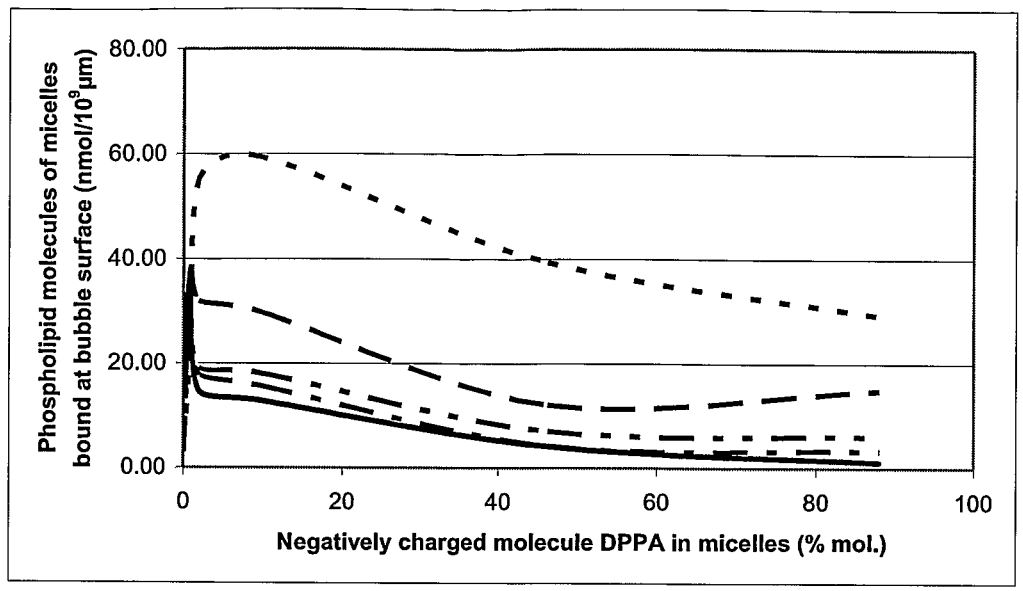
FIG. 1 is a graph showing the composition of different assemblies formed by microvesicles and MACs comprising the same materials but in different amounts.

An assembly according to the invention typically comprises a first component (also identified as the "carrier" component) in the form of a gas-filled microvesicle bearing an overall net charge and a second component associated with said carrier component (MAC) having a diameter of less than 100 nm, which bears an overall net charge of opposite sign with respect to the first component and which comprises at least one surface active agent, in particular an emulsifying agent and/or a dispersing agent, more preferably an amphiphilic compound.

Preferably, the MAC contains a desired targeting ligand, a bioactive agent, a diagnostic agent or any combination thereof.

The microvesicle's associated component (MAC) is preferably in the form of a stable supermolecular structure formed by the association of a plurality of molecules of one or more surface active agent. Preferably, said supermolecular structure comprises at least one surface active agent bearing a net charge, more preferably a ionic surface active agent. Said stable supermolecular structure can for instance be determined by a hydrophobic interaction between the hydrophobic portions of said molecules. According to a particularly preferred embodiment, the MAC is in the form of a micelle. Alternatively, said MAC can be formed by a single molecule of a polymeric ionic surfactant, optionally functionalized to include a suitable targeting, bioactive and/or diagnostic moiety The assembly of the invention is useful for preparing a pharmaceutically active formulation for use in diagnostic and/or therapeutic methods.

The term "pharmaceutically active formulation" includes within its meaning any formulation, or precursor thereof, including diagnostically, bioactive and/or therapeutically active formulations, capable of exerting a pharmaceutical effect (e.g. a diagnostic, bioactive and/or therapeutic effect) when administered in an effective amount to a patient in need thereof. Similarly, the term "pharmaceutical active" when referred to a compound, an agent or kit includes within its meaning diagnostic, bioactive and/or therapeutic compounds, agents or kits.

The term "targeting ligand" includes within its meaning any compound, moiety or residue having, or being capable to promote, a targeting activity of the assembly of the invention towards any biological or pathological site within a living body. Targets to which targeting ligand may be associated include tissues such as, for instance, myocardial tissue (including myocardial cells and cardiomyocytes), membranous tissues (including endothelium and epithelium), laminae, connective tissue (including interstitial tissue) or tumors; blood clots; and receptors such as, for instance, cell-surface receptors for peptide hormones, neurotransmitters, antigens, complement fragments, and immunoglobulins and cytoplasmic receptors for steroid hormones.

The term "bioactive agent" includes within its meaning any substance, composition or particle which may be used in any therapeutic application, such as in methods for the treatment of a disease in a patient, as well as any substance which is capable of exerting or responsible to exert a biological effect in vitro and/or in vivo. Examples of bioactive agents are drugs, pharmaceuticals, proteins, natural or synthetic peptides, including oligopeptides and polypeptides, vitamins, steroids and genetic material, including nucleosides, nucleotides and polynucleotides. A therapeutic method or treatment of a patient typically includes the use of a bioactive agent.

The term "diagnostic agent" includes within its meaning any compound, composition or particle which may be used in connection with diagnostic methods, including imaging of an internal region of a patient and/or diagnosing the presence or absence of a disease in a patient. Exemplary diagnostic agents include, for example, contrast agents for use in connection with magnetic resonance imaging, X-ray imaging, in particular computed tomography, optical imaging, nuclear imaging or molecular imaging of a patient including, for example, magnetite nanoparticles.

"Biocompatible" or "physiologically acceptable" refers to any compound, material or formulation which can be administered, in a selected amount, to a patient without negatively affecting or substantially modifying its organism's healthy or normal functioning (e.g. without determining any status of unacceptable toxicity, causing any extreme or uncontrollable allergenic response or determining any abnormal pathological condition or disease status).

The term "surface active agent" refers to any compound which is capable of stabilizing mixtures of otherwise generally immiscible materials, such as mixtures of two immiscible liquids (e.g. water and oil), mixtures of liquids with gases (e.g. gas microbubbles in water) or mixtures of liquids with insoluble particles (e.g. metal nanoparticles in water). These compounds are also generally referred to in the art as "emulsifying agents" or "dispersing agents". Preferably said compound is an "amphiphilic compound", i.e. a compound having a molecule with a hydrophilic polar head (e.g. a polar or ionic group) and a hydrophobic organic tail (e.g. a hydrocarbon chain). Examples of surface active agent, in particular of emulsifying and/or dispersing agents, are: ($C_2$-$C_{10}$) organic acids, organic fatty acids comprising a ($C_{12}$-$C_{24}$), preferably a ($C_{14}$-$C_{22}$), aliphatic chain, the pharmaceutically acceptable (alkali) salts thereof and the respective esters with polyoxyethylene, such as palmitic acid, stearic acid, arachidonic acid, oleic acid, sodium dodecanoate, sodium oxalate or sodium tartrate or polyoxyethylene fatty acid stearate; polyionic (alkali) salts, such as sodium citrate, sodium polyacrylate, sodium phosphate; organic amines, amides, quaternary amine (halide) salts, preferably containing a ($C_8$-$C_{22}$) hydrocarbon chain, including polyoxyethylated derivative thereof, such as ethanolamine, triethanolamine, alkylamines, alkanolamides, trimethylalkylamine chloride, polyoxyethylated alkylamines, polyoxyethylated alkanolamides; aminoacids; phospholipids, such as fatty acids di-esters of phosphatidylcholine, ethylphosphatidylcholine, phosphatidylglycerol, phosphatidic acid, phosphatidylethanolamine, phosphatidylserine or of sphingomyelin; esters of mono- or oligo-saccharides with ($C_{12}$-$C_{24}$), preferably a ($C_{14}$-$C_{22}$), organic fatty acids, such as sorbitan laurate; polymeric surfactants, i.e. block copolymers including hydrophobic and hydrophilic portions, such as ethyleneoxide/propyleneoxide block copolymers; organic sulfonates such as alkali (e.g. sodium) ($C_{12}$-$C_{24}$)alkyl, preferably ($C_{14}$-$C_{22}$)alkyl, sulfonates; perfluoroorganic acids, such as perfluorooctanoic acid; and mixtures thereof. Because of its nanometric dimensions, the MAC will also be referred to as the nanocomponent of the assembly, as opposed to microvesicles having micrometric dimensions. Microvesicles typically have dimensions of at least 0.5 µm, preferably of 0.8 µm and up to e.g. 20 µm, more preferably from about 1 to 8 µm; the respective mean diameter in number of microvesicles ($D_N$), measured e.g. by means of a Coulter Counter, is preferably of at least 0.8 µm, more preferably of at least 1 µm (up to about e.g. 8 µm) and much more preferably from about 1 µm to about 5 µm.

In general, depending on the respective method of preparation, microvesicles and MACs are obtained as a population of particles having a more or less narrowly distribution of dimensions. Thus, for comparing different populations of microvesicles or MACs, mean values of said distribution are generally used. As known by those skilled in the art, the dimensions of micro/nano particles and their respective size distribution can be characterized by a number of parameters, the most frequently used being the mean diameter in number $D_N$, the median diameter in number $D_{N50}$, the mean diameter in volume $D_V$ and the median diameter in volume $D_{V50}$. While diameters in number provide an indication of the mean number dimension of the particles, the diameter in volume provides information on how the total volume of the particles is distributed among the whole population. As the presence of very few large volume particles in a population of otherwise small volume particles may cause the corresponding $D_V$ value to be shifted towards high values, it is sometimes more convenient to use the $D_{V50}$ value for evaluating the distribution of a particles' population. $D_{V50}$ is a calculated value indicating that half of the total of particles' internal volume is present in particles having a diameter lower than $D_{V50}$; this allows to reduce the effects of accidentally formed large volume particles in the evaluation of the size distribution. Clearly, mono-sized particles show identical $D_N$, $D_{N50}$, $D_V$ and $D_{V50}$ values. On the other side, an increasing broadening of particles' distribution will result in a larger difference between these various values with a corresponding variation of the respective ratio thereof (e.g. increase of $D_V/D_N$ ratio). For example, particles populations containing primarily small particles (e.g. particles with a diameter around 2 μm) with nevertheless a small percentage of large particles (for instance particles with a diameter above 8 μm) show higher $D_V$ or $D_{V50}$ values as compared to the $D_N$ value, with correspondingly higher $D_V/D_N$ or $D_{V50}/D_N$ ratios.

The electrostatic interaction between the two components of the assembly is basically obtained by using a first molecular compound (comprised in the microvesicle's envelope) bearing a first net charge and a second molecular compound (comprised in the structure of the MAC) bearing a second net charge, which is opposite in sign to the first one. The microvesicles having a first overall net charge and the MAC having a second overall net charge, opposite in sign to the first one, are then associated to each other through an electrostatic interaction to obtain an assembly according to the invention.

The gas-filled microvesicle forming the first component of an assembly according to the present invention can be any microvesicle known in the art bearing an overall net charge. Preferred examples of microvesicles are microbubbles and microballoons (or microcapsules).

Microbubbles

A first example of suitable gas-filled microvesicle will be referred to hereinafter as "gas-filled microbubble".

Gas-filled microbubbles useful for preparing an assembly according to the present invention are generally bubbles of gas dispersed in an aqueous suspension which are stabilized by a (very thin) envelope comprising an amphiphilic (film-forming) compound, disposed at the gas to liquid interface. Said stabilizing envelope, sometimes referred to as an "evanescent envelope" in the art, has in general a thickness of less than 5 nm, typically of about 2-3 nm, thus often amounting to a substantially monomolecular layer. At least a portion of the amphiphilic material comprised in the envelope is composed of charged molecules, so to confer the desired overall net charge to the microbubble's envelope.

The amphiphilic compound included in the microvesicles' envelope can be a synthetic or naturally-occurring biocompatible compound and may include, for example a film forming lipid, in particular a phospholipid. Examples of amphiphilic compounds include, for instance phospholipids; lysolipids; fatty acids, such as palmitic acid, stearic acid, arachidonic acid or oleic acid; lipids bearing polymers, such as chitin, hyaluronic acid, polyvinylpyrrolidone or polyethylene glycol (PEG), also referred as "pegylated lipids"; lipids bearing sulfonated mono- di-, oligo- or polysaccharides; cholesterol, cholesterol sulfate or cholesterol hemisuccinate; tocopherol hemisuccinate; lipids with ether or ester-linked fatty acids; polymerized lipids; diacetyl phosphate; dicetyl phosphate; stearylamine; ceramides; polyoxyethylene fatty acid esters (such as polyoxyethylene fatty acid stearates), polyoxyethylene fatty alcohols, polyoxyethylene fatty alcohol ethers, polyoxyethylated sorbitan fatty acid esters, glycerol polyethylene glycol ricinoleate, ethoxylated soybean sterols, ethoxylated castor oil or ethylene oxide (EO) and propylene oxide (PO) block copolymers; sterol aliphatic acid esters including, cholesterol butyrate, cholesterol iso-butyrate, cholesterol palmitate, cholesterol stearate, lanosterol acetate, ergosterol palmitate, or phytosterol n-butyrate; sterol esters of sugar acids including cholesterol glucuronides, lanosterol glucuronides, 7-dehydrocholesterol glucoronide, ergosterol glucoronide, cholesterol gluconate, lanosterol gluconate, or ergosterol gluconate; esters of sugar acids and alcohols including lauryl glucoronide, stearoyl glucoronide, myristoyl glucoronide, lauryl gluconate, myristoyl gluconate, or stearoyl gluconate; esters of sugars with aliphatic acids including sucrose laurate, fructose laurate, sucrose palmitate, sucrose stearate, glucuronic acid, gluconic acid or polyuronic acid; saponins including sarsasapogenin, smilagenin, hederagenin, oleanolic acid, or digitoxigenin; glycerol or glycerol esters including glycerol tripalmitate, glycerol distearate, glycerol tristearate, glycerol dimyristate, glycerol trimyristate, glycerol dilaurate, glycerol trilaurate, glycerol dipalmitate, long chain alcohols including n-decyl alcohol, lauryl alcohol, myristyl alcohol, cetyl alcohol, or n-octadecyl alcohol; 6-(5-cholesten-3β-yloxy)-1-thio-β-D-galactopyranoside; digalactosyldiglyceride; 6-(5-cholesten-3β-yloxy)hexyl-6-amino-6-deoxy-1-thio-β-D-galactopyranoside; 6-(5-cholesten-3β-yloxy) hexyl-6-amino-6-deoxyl-1-thio-β-D-mannopyranoside; 12-(((7'-diethylaminocoumarin-3-yl)carbonyl)methylamino) octadecanoic acid; N-[12-(((7'-diethylaminocoumarin-3-yl) carbonyl)methylamino)octadecanoyl]-2-aminopalmitic acid; N-succinyl-dioleylphosphatidylethanolamine; 1,2-dioleyl-sn-glycerol; 1,2-dipalmitoyl-sn-3-succinylglycerol; 1,3-dipalmitoyl-2-succinylglycerol; 1-hexadecyl-2-palmitoylglycerophosphoethanolamine or palmitoylhomocysteine; alkylammonium salts comprising at least one ($C_{10}$-$C_{20}$), preferably ($C_{14}$-$C_{18}$), alkyl chain, such as, for instance, stearylammonium chloride, hexadecylammonium chloride, dimethyldioctadecylammonium bromide (DDAB), hexadecyltrimethylammonium bromide (CTAB); tertiary or quaternary ammonium salts comprising one or preferably two ($C_{10}$-$C_{20}$), preferably ($C_{14}$-$C_{18}$), acyl chain linked to the N-atom through a ($C_3$-$C_6$) alkylene bridge, such as, for instance, 1,2-distearoyl-3-trimethylammonium-propane (DSTAP), 1,2-dipalmitoyl-3-trimethylammonium-propane (DPTAP), 1,2-oleoyl-3-trimethylammonium-propane (DOTAP), 1,2-distearoyl-3-dimethylammonium-propane (DSDAP): and mixtures or combinations thereof.

Depending on the combination of components and on the manufacturing process of the microbubbles, the above listed exemplary compounds may be employed as main compound for forming the microvesicle's envelope or as simple additives, thus being present only in minor amounts.

According to a preferred embodiment, at least one of the compounds forming the microvesicles' envelope is a phospholipid, optionally in admixture with any of the other above cited film-forming materials. According to the present description, the term phospholipid is intended to encompass any amphiphilic phospholipid compound, the molecules of which are capable of forming a stabilizing film of material (typically in the form of a mono-molecular layer) at the gas-water boundary interface in the final microbubbles suspension. Accordingly, these materials are also referred to in the art as "film-forming phospholipids".

Amphiphilic phospholipid compounds typically contain at least one phosphate group and at least one, preferably two, lipophilic long-chain hydrocarbon group.

Examples of suitable phospholipids include esters of glycerol with one or preferably two (equal or different) residues of fatty acids and with phosphoric acid, wherein the phosphoric acid residue is in turn bound to a hydrophilic group, such as choline (phosphatidylcholines—PC), serine (phosphatidylserines—PS), glycerol (phosphatidylglycerols—PG), ethanolamine (phosphatidylethanolamines—PE), inositol (phosphatidylinositol), and the like groups. Esters of phospholipids with only one residue of fatty acid are generally referred to in the art as the "lyso" forms of the phospholipid. Fatty acids residues present in the phospholipids are in general long chain aliphatic acids, typically containing from 12 to 24 carbon atoms, preferably from 14 to 22; the aliphatic chain may contain one or more unsaturations or is preferably completely saturated. Examples of suitable fatty acids included in the phospholipids are, for instance, lauric acid, myristic acid, palmitic acid, stearic acid, arachidic acid, behenic acid, oleic acid, linoleic acid, and linolenic acid. Preferably, saturated fatty acids such as myristic acid, palmitic acid, stearic acid and arachidic acid are employed.

Further examples of phospholipid are phosphatidic acids, i.e. the diesters of glycerol-phosphoric acid with fatty acids; sphingolipids such as sphingomyelins, i.e. those phosphatidylcholine analogs where the residue of glycerol diester with fatty acids is replaced by a ceramide chain; cardiolipins, i.e. the esters of 1,3-diphosphatidylglycerol with a fatty acid; glycolipids such as gangliosides GM1 (or GM2) or cerebrosides; glucolipids; sulfatides and glycosphingolipids.

As used herein, the term phospholipids include either naturally occurring, semisynthetic or synthetically prepared products that can be employed either singularly or as mixtures.

Examples of naturally occurring phospholipids are natural lecithins (phosphatidylcholine (PC) derivatives) such as, typically, soya bean or egg yolk lecithins.

Examples of semisynthetic phospholipids are the partially or fully hydrogenated derivatives of the naturally occurring lecithins. Preferred phospholipids are fatty acids di-esters of phosphatidylcholine, ethylphosphatidylcholine, phosphatidylglycerol, phosphatidic acid, phosphatidylethanolamine, phosphatidylserine or of sphingomyelin.

Examples of preferred phospholipids are, for instance, dilauroyl-phosphatidylcholine (DLPC), dimyristoyl-phosphatidylcholine (DMPC), dipalmitoyl-phosphatidylcholine (DPPC), diarachidoyl-phosphatidylcholine (DAPC), distearoyl-phosphatidylcholine (DSPC), dioleoyl-phosphatidylcholine (DOPC), 1,2 Distearoyl-sn-g lycero-3-Ethyl phosphocholine (Ethyl-DSPC), dipentadecanoyl-phosphatidylcholine (DPDPC), 1-myristoyl-2-palmitoyl-phosphatidylcholine (MPPC), 1-palmitoyl-2-myristoyl-phosphatidylcholine (PMPC), 1-palmitoyl-2-stearoyl-phosphatidylcholine (PSPC), 1-stearoyl-2-palmitoyl-phosphatidylcholine (SPPC,), 1-palmitoyl-2-oleylphosphatidylcholine (POPC), 1-oleyl-2-palmitoyl-phosphatidylcholine (OPPC), dilauroyl-phosphatidylglycerol (DLPG) and its alkali metal salts, diarachidoylphosphatidylglycerol (DAPG) and its alkali metal salts, dimyristoylphosphatidylglycerol (DMPG) and its alkali metal salts, dipalmitoylphosphatidylglycerol (DPPG) and its alkali metal salts, distearoylphosphatidylglycerol (DSPG) and its alkali metal salts, dioleoyl-phosphatidylglycerol (DOPG) and its alkali metal salts, dimyristoyl phosphatidic acid (DMPA) and its alkali metal salts, dipalmitoyl phosphatidic acid (DPPA) and its alkali metal salts, distearoyl phosphatidic acid (DSPA), diarachidoyl-phosphatidic acid (DAPA) and its alkali metal salts, dimyristoylphosphatidylethanolamine (DMPE), dipalmitoylphosphatidylethanolamine (DPPE), distearoyl phosphatidylethanolamine (DSPE), dioleylphosphatidylethanolamine (DOPE), diarachidoylphosphatidylethanolamine (DAPE), dilinoleylphosphatidylethanolamine (DLPE), dimyristoyl phosphatidylserine (DMPS), diarachidoyl phosphatidylserine (DAPS), dipalmitoyl phosphatidylserine (DPPS), distearoylphosphatidylserine (DSPS), dioleoylphosphatidylserine (DOPS), dipalmitoyl sphingomyelin (DPSP), and distearoylsphingomyelin (DSSP).

The term phospholipid further includes modified phospholipid, e.g. phospholipids where the hydrophilic group is in turn bound to another hydrophilic group. Examples of modified phospholipids are phosphatidylethanolamines modified with polyethylenglycol (PEG), i.e. phosphatidylethanolamines where the hydrophilic ethanolamine moiety is linked to a PEG molecule of variable molecular weight e.g. from 300 to 5000 daltons), such as DPPE-PEG or DSPE-PEG, i.e. DPPE (or DSPE) having a PEG polymer attached thereto. For example, DPPE-PEG2000 refers to DPPE having attached thereto a PEG polymer having a mean average molecular weight of about 2000.

Particularly preferred phospholipids are DAPC, DSPC, DPPA, DSPA, DMPS, DPPS, DSPS and Ethyl-DSPC. Most preferred are DAPC or DSPC.

Mixtures of phospholipids can also be used, such as, for instance, mixtures of DPPC, DSPC and/or DAPC with DSPS, DPPS, DSPA, DPPA, DSPG, DPPG, Ethyl-DSPC and/or Ethyl-DPPC, In some embodiments the phospholipid is the main component of the stabilizing envelope of microbubbles, amounting to at least 50% (w/w) of the total amount of components forming the envelope of the gas filled microbubbles. In some preferred embodiments, substantially the totality of the envelope (i.e. at least 90% and up to 100% by weight) can be formed of phospholipids.

The phospholipids can conveniently be used in admixture with any of the above listed amphiphilic compounds. Thus, for instance, lipids such as cholesterol, ergosterol, phytosterol, sitosterol, lanosterol, tocopherol, propyl gallate or ascorbyl palmitate, fatty acids such as myristic acid, palmitic acid, stearic acid, arachidic acid and derivatives thereof or butylated hydroxytoluene and/or other non-phospholipid compounds can optionally be added to one or more of the foregoing phospholipids in proportions ranging from zero to 50% by weight, preferably up to 25%. Particularly preferred is palmitic acid.

In order to confer the desired overall net charge to the microbubble, the envelope shall comprise at least one component bearing an overall net charge, in particular a charged amphiphilic material, preferably a lipid or a phospholipid.

Examples of phospholipids bearing an overall negative charge are derivatives, in particular fatty acid di-esters, of phosphatidylserine, such as DMPS, DPPS, DSPS; of phosphatidic acid, such as DMPA, DPPA, DSPA; of phosphatidylglycerol such as DMPG, DPPG and DSPG. Also modified phospholipids, in particular PEG-modified phosphatidylethanolamines, such as DMPE-PEG2000, DMPE-PEG3000, DMPE-PEG4000, DPPE-PEG5000, DPPE-PEG2000, DPPE-PEG3000, DPPE-PEG4000, DPPE-PEG5000, DSPE-PEG2000, DSPE-PEG3000, DSPE-PEG4000, DSPE-PEG5000, DAPE-PEG2000, DAPE-PEG3000, DAPE-PEG4000 or DAPE-PEG5000 can be used as negatively charged molecules. Also the lyso-form of the above cited phospholipids, such as lysophosphatidylserine derivatives (e.g. lyso-DMPS, -DPPS or -DSPS), lysophosphatidic acid derivatives (e.g. lyso-DMPA, -DPPA or -DSPA) and lysophosphatidylglycerol derivatives (e.g. lyso-DMPG, -DPPG or -DSPG), can advantageously be used as negatively charged compound. Examples of negatively charged lipids are bile acid salts such as cholic acid salts, deoxycholic acid salts or glycocholic acid salts; and ($C_{12}$-$C_{24}$), preferably ($C_{14}$-$C_{22}$) fatty acid salts such as, for instance, palmitic acid salt, stearic acid salt, 1,2-dipalmitoyl-sn-3-succinylglycerol salt or 1,3-dipalmitoyl-2-succinylglycerol salt.

Preferably, the negatively charged compound is selected among DPPA, DPPS, DSPG, DSPE-PEG2000, DSPE-PEG5000 or mixtures thereof.

The negatively charged component is typically associated with a corresponding positive counter-ion, which can be mono- (e.g. an alkali metal or ammonium), di- (e.g. an earth-alkali metal) or tri-valent (e.g. aluminium). Preferably the counter-ion is selected among alkali metal cations, such as $Li^+$, $Na^+$, or $K^+$, more preferably $Na^+$.

Examples of phospholipids bearing an overall positive charge are derivatives of ethylphosphatidylcholine, in particular esters of ethylphosphatidylcholine with fatty acids, such as 1,2-Distearoyl-sn-glycero-3-Ethylphosphocholine (Ethyl-DSPC or DSEPC), 1,2-Dipalmitoyl-sn-glycero-3-Ethylphosphocholine (Ethyl-DPPC or DPEPC). The negative counterion is preferably an halogen ion, in particular chlorine or bromine. Examples of positively charged lipids are alkylammonium salts with a halogen counter ion (e.g. chlorine or bromine) comprising at least one ($C_{10}$-$C_{20}$), preferably ($C_{14}$-$C_{18}$), alkyl chain, such as, for instance stearylammonium chloride, hexadecylammonium chloride, dimethyldioctadecylammonium bromide (DDAB), hexadecyltrimethylammonium bromide (CTAB). Further examples of positively charged lipids are tertiary or quaternary ammonium salts with a halogen counter ion (e.g. chlorine or bromine) comprising one or preferably two ($C_{10}$-$C_{20}$), preferably ($C_{14}$-$C_{18}$), acyl chain linked to the N-atom through a ($C_3$-$C_6$) alkylene bridge, such as, for instance, 1,2-distearoyl-3-trimethylammonium-propane (DSTAP), 1,2-dipalmitoyl-3-trimethylammonium-propane (DPTAP), 1,2-oleoyl-3-trimethylammonium-propane (DOTAP), 1,2-distearoyl-3-dimethylammonium-propane (DSDAP).

DSEPC, DPEPC and/or DSTAP are preferably employed as positively charged compounds in the microvesicle's envelope.

The positively charged component is typically associated with a corresponding negative counter-ion, which can be mono- (e.g. halogen), di- (e.g. sulphate) or tri-valent (e.g. phosphate). Preferably the counter-ion is selected among halogen ions, such as $F^-$ (fluorine), $Cl^-$ (chlorine) or $Br^-$ (bromine).

In order to allow an effective electrostatic interaction with the MAC, the total amount of charged compounds in the microvesicle's envelope should be of at least 1% by mole with respect to the total amount of material forming said envelope, preferably of at least 5% and much more preferably of at least 10%. In some preferred combinations of microvesicles and MACs, it has been observed that an amount of at least 20%, preferably of at least 40%, of charged compounds in the microvesicles' envelope allows binding relatively higher amounts of MACs to said microvesicles. Although in some embodiments the totality of the envelope of the microvesicle can be formed by charged compounds, it has been observed that it may be advantageous to add at least minimum amounts of neutral compounds to the formulation forming said envelope. Preferably, the total amount of charged component can thus be equal to or lower than about 95% by mole with respect to the total amount of components forming the envelope of the microvesicle, more preferably equal to or lower than 90%, down to particularly preferred amounts equal to or lower than 80%.

Mixtures of neutral and charged phospholipids and/or charged lipids can be satisfactorily employed to form the microvesicles of an assembly of the present invention. Preferably, mixtures of two or more lipids or phospholipids, at least one with a neutral charge and at least one with an overall net charge, are employed. More preferably, mixtures of two or more lipids or phospholipids, at least one with neutral and at least one with positive charge are employed, to obtain microvesicles with an overall positive charge. The amount of charged lipid or phospholipid may vary from about 95% to about 1% by mole, with respect to the total amount of lipid and phospholipid, preferably from 80% to 20% by mole.

Preferred mixtures of neutral phospholipids and charged lipids or phospholipids are, for instance, DPPG/DSPC, DSTAP/DAPC, DPPS/DSPC, DPPS/DAPC, DSPA/DAPC, DSPA/DSPC and DSPG/DSPC.

Other excipients or additives may be present either in the dry formulation or may be added together with the aqueous carrier used for the reconstitution, without necessarily being involved (or only partially involved) in the formation of the stabilizing envelope of the microvesicle. These include pH regulators, osmolality adjusters, viscosity enhancers, emulsifiers, bulking agents, etc. and may be used in conventional amounts. For instance compounds like polyoxypropylene glycol and polyoxyethylene glycol as well as copolymers thereof can be used. Examples of viscosity enhancers or stabilizers are compounds selected from linear and cross-linked poly- and oligo-saccharides, sugars, hydrophilic polymers like polyethylene glycol.

As the preparation of gas-filled microvesicles may involve a freeze drying or spray drying step, it may be advantageous to include in the formulation one or more agents with cryoprotective and/or lyoprotective effect and/or one or more bulking agents, for example an amino-acid such as glycine; a carbohydrate, e.g. a sugar such as sucrose, mannitol, maltose, trehalose, glucose, lactose or a cyclodextrin, or a polysaccharide such as dextran; or a polyglycol such as polyethylene glycol.

The microbubbles usable in an assembly according to the invention can be produced according to any known method in the art. Typically, the manufacturing method involves the preparation of a dried powdered material comprising an amphiphilic material as above indicated, preferably by lyophilization (freeze drying) of an aqueous or organic suspension comprising said material.

For instance, as described in WO 91/15244 film-forming amphiphilic compounds can be first converted into a lamellar form by any liposome forming method. For instance, an aqueous solution comprising the film forming lipids and optionally other additives (e.g. viscosity enhancers, non-film forming surfactants, electrolytes etc.) can be submitted to high-speed mechanical homogenisation or to sonication under acoustical or ultrasonic frequencies, and then freeze dried to form a free flowable powder which is then stored in the presence of a gas. Optional washing steps, as disclosed for instance in U.S. Pat. No. 5,597,549, can be performed before freeze drying.

According to an alternative embodiment (described for instance in the above cited U.S. Pat. No. 5,597,549) a film forming compound and a hydrophilic stabiliser (e.g. polyethylene glycol, polyvinyl pyrrolidone, polyvinyl alcohol, glycolic acid, malic acid or maltol) can be dissolved in an organic solvent (e.g. tertiary butanol, 2-methyl-2-butanol or $C_2Cl_4F_2$) and the solution can be freeze-dried to form a dry powder.

Alternatively, as disclosed in the above cited WO 04/069284, a phospholipid (selected among those cited above and including at least one of the above-identified charged phospholipids) and a lyoprotecting agent (such as those previously listed, in particular carbohydrates, sugar alcohols, polyglycols and mixtures thereof) can be dispersed in an emulsion of water with a water immiscible organic solvent (e.g. branched or linear alkanes, alkenes, cycloalkanes, aromatic hydrocarbons, alkyl ethers, ketones, halogenated hydrocarbons, perfluorinated hydrocarbons or mixtures thereof). The so obtained emulsion, which contains microdroplets of solvent surrounded and stabilized by the phospholipid material (and optionally by other amphiphilic film-forming compounds), is then lyophilized according to conventional techniques to obtain a lyophilized material, which is stored (e.g. in a vial in the presence of a suitable gas) and which can be reconstituted with an aqueous carrier to finally give a gas-filled microbubbles suspension.

A further process for preparing gas-filled microbubbles comprises generating a gas microbubble dispersion by submitting an aqueous medium comprising a phospholipid (and optionally other amphiphilic film-forming compounds and/or additives) to a controlled high agitation energy (e.g. by means of a rotor stator mixer) in the presence of a desired gas and subjecting the obtained dispersion to lyophilisation to yield a dried reconstitutable product.

An example of this process is given, for instance, in WO 97/29782, here enclosed by reference.

Spray drying techniques (as disclosed for instance in U.S. Pat. No. 5,605,673) can also be used to obtain the dried powder containing the microvesicles of the assembly of the invention.

The dried or lyophilised product obtained with any of the above techniques will generally be in the form of a powder or a cake, and can be stored (e.g. in a vial) in contact with the desired gas. The product is readily reconstitutable in a suitable aqueous liquid carrier, which is physiologically acceptable, sterile and injectable, to form the gas-filled microvesicles. Suitable liquid carriers are water, aqueous solutions such as saline (which may advantageously be balanced so that the final product for injection is not hypotonic), or solutions of one or more tonicity adjusting substances such as salts or sugars, sugar alcohols, glycols or other non-ionic polyol materials (eg. glucose, sucrose, sorbitol, mannitol, glycerol, polyethylene glycols, propylene glycols and the like).

Microballoons

Other gas-filled microvesicles suitable for an assembly according to the invention are referred to in the art as "microballoons". In general, these gas-filled microvesicles have a material envelope, the thickness of which is greater than the thickness of microbubbles' stabilizing film-envelope. Depending from the material forming said envelope (which can be e.g. polymeric, proteinaceous, of a water insoluble lipid or of any combination thereof), said thickness is in general of at least 50 nm, typically of at least 100 nm, up to few hundred nanometers (e.g. 300 nm).

Microballoons also generally differ from microbubbles in terms of acoustic response to ultrasonication. While the ultrasonic behavior of microbubbles is in fact closer to the behavior of "free" gas bubbles, microballoons (probably because of a higher stiffness of the envelope) are in general less responsive (in terms of intensity of the reflected echo signal) when irradiated at low levels of acoustic pressure energy (e.g. at a mechanical index of about 0.1).

Examples of microballoons which are useful for preparing an assembly according to the invention are preferably microballoons having a polymeric envelope, preferably comprising a biodegradable polymer, or an envelope based on biodegradable water-insoluble lipids, such as, for instance those described in U.S. Pat. Nos. 5,711,933 and 6,333,021, herein incorporated by reference in their entirety. Microballoons having a proteinaceous envelope, i.e. made of natural proteins (albumin, haemoglobin) such as those described in U.S. Pat. No. 4,276,885 or EP-A-0 324 938, can also be employed Polymers forming the envelope of the injectable microballoons are preferably hydrophilic, biodegradable physiologically compatible polymers. Examples of such polymers, which may be natural or synthetic, are substantially insoluble polysaccharides (e.g. chitosan or chitin), polycyanoacrylates, polylactides and polyglycolides and their copolymers, copolymers of lactides and lactones such as γ-caprolactone or δ-valerolactone, copolymers of ethyleneoxide and lactides, polyethyleneimines, polypeptides, and proteins such as gelatin, collagen, globulins or albumins. Other suitable polymers mentioned in the above cited U.S. Pat. No. 5,711,933 include poly-(ortho)esters, polylactic and polyglycolic acid and their copolymers (e.g. DEXON®, Davis & Geck, Montreal, Canada); poly(DL-lactide-co-γ-caprolactone), poly(DL-lactide-co-δ-valerolactone), poly(DL-lactide-co-γ-butyrolactone), polyalkylcyanoacrylates; polyamides, polyhydroxybutyrate; polydioxanone; poly-β-aminoketones; polyphosphazenes; and polyanhydrides. Polyamino-acids such as polyglutamic and polyaspartic acids can also be used, as well as their derivatives, such as partial esters with lower alcohols or glycols. Copolymers with other amino acids such as methionine, leucine, valine, proline, glycine, alanine, etc. can also be used. Derivatives of polyglutamic and polyaspartic acid with controlled biodegradability (such as those described in WO87/03891, U.S. Pat. No. 4,888,398 or EP 130935, all herein incorporated by reference) can also be used. These polymers (and copolymers with other amino-acids) have formulae of the following type: —(NH—CHA—CO)$_w$—(NH—CHX—CO)$_y$— where X designates the side chain of an amino acid residue (e.g. methyl, isopropyl, isobutyl, or benzyl); A is a group of formula —(CH$_2$)$_n$COOR$^1$R$^2$—OCOR, —(CH$_2$)$_n$COO—CHR$^1$COOR, —(CH$_2$)$_n$CO(NH—CHX—CO)$_m$NH—CH(COOH)—(CH$_2$)$_p$COOH, or the respective anhydrides thereof, wherein R$^1$ and R$^2$ represent H or lower alkyls, and R represents alkyl or aryl; or R and R$^1$ are connected together by a substituted or unsubstituted linking member to provide 5- or 6-membered rings; n, m and p are lower integers, not exceeding 5; and w and y are integers selected for having molecular weights not below 5000.

Non-biodegradable polymers (e.g. for making microballoons to be used in the digestive tract) can be selected from most water-insoluble, physiologically acceptable, bioresistant polymers including polyolefins (polystyrene), acrylic resins (polyacrylates, polyacrylonitrile), polyesters (polycarbonate), polyurethanes, polyurea and their copolymers. ABS (acryl-butadiene-styrene) is a preferred copolymer.

Biodegradable water-insoluble lipids useful for forming a microballoon for an assembly according to the invention comprise, for instance, solid water insoluble mono-, di- or tri-glycerides, fatty acids, fatty acid esters, sterols such as cholesterol, waxes and mixtures thereof. Mono-, di- and tri-glycerides include mainly the mono-, di- and tri-laurin compounds as well as the corresponding—myristin, -palmitin, -stearin, -arachidin and -behenin derivatives. Mono-, di- and tri-myristin, -palmitin -stearin and mixed triglycerides such as dipalmitoylmonooleyl glyceride are particularly useful; tripalmitin and tristearin are preferred. Fatty acids include solid (at room temperature, about 18-25° C.) fatty acids (preferably saturated) having 12 carbon atoms or more, including, for instance, lauric, arachidic, behenic, palmitic, stearic, sebacic, myristic, cerotinic, melissic and erucic acids and the fatty acid esters thereof. Preferably, the fatty acids and their esters are used in admixture with other glycerides.

The sterols are preferably used in admixture with the other glycerides and or fatty acids and are selected from cholesterol, phytosterol, lanosterol, ergosterol, etc. and esters of the sterols with the above mentioned fatty acids; however, cholesterol is preferred.

Preferred biodegradable lipids are triglycerides such as tripalmitin, tristearin or mixtures of the above mentioned triglycerides.

Optionally, up to 75% by weight of a biodegradable polymer, such as those listed previously, can be admixed together with the biodegradable water insoluble lipid forming the envelope of the microballoon.

Advantageously, ionic polymers (i.e. polymers bearing ionic moieties in their structure), preferably biodegradable ionic polymers, can also be used to form the stabilizing envelope of the microballoons, thus conferring the desired overall net charge thereto. Ionic polymers can be used as main components of the stabilizing envelope or they can be admixed in various amounts (e.g. from 2 to 80% by weight) with non ionic polymers. Suitable ionic polymers are, for instance, polymers comprising a quaternized nitrogen atom, such as quaternized amines or polymers comprising an carboxylic, sulfate, sulfonate or phosphonate moieties. Examples of suitable ionic polymers include, without limitation, Polyethylenimine, poly(diallyldimethylammonium chloride), poly{bis(2-chloroethyl)ether-alt-1,3-bis[3-(dimethylamino)propyl]urea} quaternized (Polyquaternium®-2), poly(4-vinylpyridinium tribromide), hydroxyethylcellulose ethoxylate quaternized (Polyquaternium®-4, poly(p-xylene tetrahydrothiophenium chloride), poly(L-lysine), chitin, diethyleneaminoethyl dextran, poly(acrylic acid), poly(methacrylic acid), poly(styrene-alt-maleic acid), poly(amino acids), alginic acid, poly(uridylic acid), hyaluronic acid, i.e. poly(β-glucuronic acid-alt-β-N-acetylclucos-amide), poly(galacturonic acid), poly(vinyl acetate-co-crotonic acid), DNA, poly(3,3',4,4'-benzophenonetetracarboxylic dianhydride-co-4,4'-oxydianiline), poly(isoprene-graft-maleic acid monomethyl ether), copolymer of glutammic acid with alkyl glutammate, heparin, poly(styrene sulfonate), sulfonated poly(isophthalic acid), poly(vinyl sulfonate, potassium salt), poly(vinyl sulfate, potassium salt), chondroitin sulfate A, dextran sulfate, fucoidan, polyphosphoric acid, sodium polyphosphate, sodium polyvinylphosphonate, poly-L-lisine hydrobromide, chitosan, chitosan sulfate, sodium alginate, alginic acid and ligninsulfonate.

Conventional additives can also be incorporated into the envelope of the microballoons, to modify physical properties thereof, such as dispersibility, elasticity and water permeability. In particular, effective amounts of amphiphilic materials can be added to the emulsion prepared for the manufacturing of said microballoons, in order to increase the stability thereof. Said materials can advantageously be selected among those amphiphilic compounds, such as lipids, phospholipids and modified phospholipids, listed in the foregoing of this specification.

The added amphiphilic material can advantageously be a compound bearing an overall net charge. Preferred charged lipids, phospholipids and modified phospholipids are those previously listed.

In order to allow an effective electrostatic interaction with the MAC, the total amount of charged additive in the envelope of the microballoon should be of at least 1% by mole with respect to the total amount of material forming said envelope. The total amount of charged component is however preferably lower than about 70% by mole with respect to the total amount of the material forming the envelope of the microballoon. Preferably the amount of charged compound is from about 2% to 40%.

Other excipients or additives, in particular used for the preparation of microballoons, can be incorporated into the envelope such as redispersing agents or viscosity enhancers.

Biodegradable polymer containing microballoons can be prepared, for instance, according to the process disclosed in U.S. Pat. No. 5,711,933, herein incorporated by reference, which comprises (a) emulsifying a hydrophobic organic phase into a water phase so as to obtain droplets of said hydrophobic phase as an oil-in-water emulsion in said water phase; (b) adding to said emulsion a solution of at least one polymer in a volatile solvent insoluble in the water phase, so that said polymer forms a layer around said droplets; (c) evaporating said volatile solvent so that the polymer deposits by interfacial precipitation around the droplets which then form beads with a core of said hydrophobic phase encapsulated by a membrane of said polymer, said beads being in suspension in said water phase; (d) removing said encapsulated hydrophobic phase by evaporation by subjecting said suspension to reduced pressure; and (e) replacing said evaporated hydrophobic phase with a suitable gas.

Biodegradable lipid containing microballoons can be prepared, for instance, according to the process disclosed in U.S. Pat. No. 6,333,021 (herein incorporated by reference), by dispersing a mixture of one or more of the solid constituents of the microcapsule envelope dissolved in an organic solvent in a water carrier phase, so as to produce an oil-in-water emulsion. The emulsion water phase may contain an effective amount of amphiphilic materials which are used to stabilise the emulsion.

A certain amount of redispersing agent and/or of a cryo-protecting or lyoprotecting agent, such as those previously indicated, is then added to the emulsion of tiny droplets of the organic solution in the water phase, prior to freezing at a temperature below −30° C. Any convenient redispersing agent may be used; redispersing agents selected from sugars, albumin, gelatine, polyvinyl pyrolidone (PVP), polyvinyl alcohol (PVA), polyethylene glycol (PEG) and ethyleneoxide-propyleneoxide block copolymer (e.g. Pluronic®, or Synperonic®) or mixtures thereof are preferred. The redispersing agents which are added to prevent particle agglomeration are particularly useful when the microcapsules are in the form of non-coalescent, dry and instantly dispersible powders. The frozen emulsion is then subjected to reduced pressure to effect lyophilisation, i.e. the removal by sublimation of the organic solvent from the droplets and of the water of the carrier phase, and the freeze-dried product is then contacted with the desired gas.

Biocompatible Gas

Any biocompatible gas, gas precursor or mixture thereof may be employed to fill the above microvesicles, the gas being selected depending on the chosen modality.

The gas may comprise, for example, air; nitrogen; oxygen; carbon dioxide; hydrogen; nitrous oxide; a noble or inert gas such as helium, argon, xenon or krypton; a radioactive gas such as $Xe^{133}$ or $Kr^{81}$; a hyperpolarized noble gas such as hyperpolarized helium, hyperpolarized xenon or hyperpolarized neon; a low molecular weight hydrocarbon (e.g. containing up to 7 carbon atoms), for example an alkane such as methane, ethane, propane, butane, isobutane, pentane or isopentane, a cycloalkane such as cyclobutane or cyclopentane, an alkene such as propene, butene or isobutene, or an alkyne such as acetylene; an ether; a ketone; an ester; halogenated gases, preferably fluorinated gases, such as or halogenated, fluorinated or prefluorinated low molecular weight hydrocarbons (e.g. containing up to 7 carbon atoms); or a mixture of any of the foregoing. Where a halogenated hydrocarbon is used, preferably at least some, more preferably all, of the halogen atoms in said compound are fluorine atoms.

Fluorinated gases are preferred, in particular perfluorinated gases, especially in the field of ultrasound imaging. Fluorinated gases include materials which contain at least one fluorine atom such as, for instance fluorinated hydrocarbons (organic compounds containing one or more carbon atoms and fluorine); sulfur hexafluoride; fluorinated, preferably perfluorinated, ketones such as perfluoroacetone; and fluorinated, preferably perfluorinated, ethers such as perfluorodiethyl ether. Preferred compounds are perfluorinated gases, such as $SF_6$ or perfluorocarbons (perfluorinated hydrocarbons), i.e. hydrocarbons where all the hydrogen atoms are replaced by fluorine atoms, which are known to form particularly stable microbubble suspensions, as disclosed, for instance, in EP 0554 213, which is herein incorporated by reference.

The term perfluorocarbon includes saturated, unsaturated, and cyclic perfluorocarbons. Examples of biocompatible, physiologically acceptable perfluorocarbons are: perfluoroalkanes, such as perfluoromethane, perfluoroethane, perfluoropropanes, perfluorobutanes (e.g. perfluoro-n-butane, optionally in admixture with other isomers such as perfluoro-isobutane), perfluoropentanes, perfluorohexanes or perfluoroheptanes; perfluoroalkenes, such as perfluoropropene, perfluorobutenes (e.g. perfluorobut-2ene) or perfluorobutadiene; perfluoroalkynes (e.g. perfluorobut-2-yne); and perfluorocycloalkanes (e.g. perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane and perfluorocycloheptane). Preferred saturated perfluorocarbons have the formula $C_nF_{n+2}$, where n is from 1 to 12, preferably from 2 to 10, most preferably from 3 to 8 and even more preferably from 3 to 6. Suitable perfluorocarbons include, for example, $CF_4$, $C_2F_6$, $C_3F_8$, $C_4F_8$, $C_4F_{10}$, $C_5F_{12}$, $C_6F_{12}$, $C_6F_{14}$, $C_7F_{14}$, $C_7F_{16}$, $C_8F_{18}$, and $C_9F_{20}$.

Particularly preferred gases are $SF_6$ or perfluorocarbons selected from $CF_4$, $C_2F_6$, $C_3F_8$, $C_4F_8$, $C_4F_{10}$ or mixtures thereof; $SF_6$, $C_3F_8$ or $C_4F_{10}$ are particularly preferred.

It may also be advantageous to use a mixture of any of the above gases in any ratio. For instance, the mixture may comprise a conventional gas, such as nitrogen, air or carbon dioxide and a gas forming a stable microbubble suspension, such as sulfur hexafluoride or a perfluorocarbon as indicated above. Examples of suitable gas mixtures can be found, for instance, in WO 94/09829, which is herein incorporated by reference. The following combinations are particularly preferred: a mixture of gases (A) and (B) in which the gas (B) is a fluorinated gas, preferably selected from $SF_6$, $CF_4$, $C_2F_6$, $C_3F_6$, $C_3F_8$, $C_4F_6$, $C_4F_8$, $C_4F_{10}$, $C_5F_{10}$, $C_5F_{12}$ or mixtures thereof, and (A) is selected from air, oxygen, nitrogen, carbon dioxide or mixtures thereof. The amount of gas (B) can represent from about 0.5% to about 95% v/v of the total mixture, preferably from about 5% to 80%.

In certain circumstances it may be desirable to include a precursor to a gaseous substance (i.e. a material that is capable of being converted to a gas in vivo). Preferably the gaseous precursor and the gas derived therefrom are physiologically acceptable. The gaseous precursor may be pH-activated, photo-activated, temperature activated, etc. For example, certain perfluorocarbons may be used as temperature activated gaseous precursors. These perfluorocarbons, such as perfluoropentane or perfluorohexane, have a liquid/gas phase transition temperature above room temperature (or the temperature at which the agents are produced and/or stored) but below body temperature; thus, they undergo a liquid/gas phase transition and are converted to a gas within the human body.

For ultrasonic echography, the biocompatible gas or gas mixture is preferably selected from air, nitrogen, carbon dioxide, helium, krypton, xenon, argon, methane, halogenated hydrocarbons (including fluorinated gases such as perfluorocarbons and sulfur hexafluoride) or mixtures thereof. Advantageously, perfluorocarbons (in particular $C_4F_{10}$ or $C_3F_8$) or $SF_6$ can be used, optionally in admixture with air or nitrogen.

For the use of the assembly in MRI the microvesicles will preferably contain a hyperpolarized noble gas such as hyperpolarized neon, hyperpolarized helium, hyperpolarized xenon, or mixtures thereof, optionally in admixture with air, $CO_2$, oxygen, nitrogen, helium, xenon, or any of the halogenated hydrocarbons as defined above.

For use in scintigraphy, the microvesicle of an assembly according to the invention will preferably contain radioactive gases such as $Xe^{133}$ or $Kr^{81}$ or mixtures thereof, optionally in admixture with air, $CO_2$, oxygen, nitrogen, helium, kripton or any of the halogenated hydrocarbons as defined above.

Microvesicle's Associated Component (MAC)

The second component of the assembly associated to the microvesicle (MAC) can be any structural entity comprising a biocompatible surface active agent bearing an overall net charge. In particular, said structural entity is preferably a supermolecular structure formed by the association of a plurality of, preferably amphiphilic, molecules. In some embodiments, said charged compound is admixed with other surface active agents and/or additives which are neutral. The MAC may further comprise a desired targeting ligand, bioactive agent and/or diagnostic agent, depending on the specific application of the assembly. Biocompatible surface active materials suitable for preparing a MAC for an assembly according to the invention can be selected among those compound previously listed, such as ($C_2$-$C_{10}$) organic acids, organic fatty acids comprising a ($C_{12}$-$C_{24}$), preferably a ($C_{14}$-$C_{22}$), aliphatic chain, the pharmaceutically acceptable (alkali) salts thereof and the respective esters with polyoxyethylene, such as palmitic acid, stearic acid, arachidonic acid, oleic acid, sodium dodecanoate, sodium oxalate or sodium tartrate or polyoxyethylene fatty acid stearate; polyionic (alkali) salts, such as sodium citrate, sodium polyacrylate, sodium phosphate; organic amines, amides, quaternary amine (halide) salts, preferably containing a ($C_8$-$C_{22}$) hydrocarbon chain, including polyoxyethylated derivative thereof, such as ethanolamine, triethanolamine, alkylamines, alkanolamides, trimethylalkylamine chloride, polyoxyethylated alkylamines, polyoxyethylated alkanolamides; aminoacids; phospholipids, such as fatty acids di-esters of phosphatidylcholine, ethylphosphatidylcholine, phosphatidylglycerol, phosphatidic acid, phosphatidylethanolamine, phosphatidylserine or of sphingomyelin; esters of mono- or oligo-saccharides with ($C_{12}$-$C_{24}$), preferably a ($C_{14}$-$C_{22}$), organic fatty acids, such as sorbitan laurate; polymeric surfactants, i.e. block copolymers including hydrophobic and hydrophilic portions, such as ethyleneoxide/propyleneoxide block copolymers; organic sulfonates such as alkali (e.g. sodium) ($C_{12}$-$C_{24}$) alkyl, preferably ($C_{14}$-$C_{22}$)alkyl, sulfonate; perfluoroorganic acids, such as perfluorooctanoic acid; and mixtures thereof. Preferred compounds are those neutral or charged amphiphilic materials previously listed among the suitable components of microbubbles, including lipids, phospholipids and modified phospholipids. A preferred MAC is in the form of a micelle.

The preparation of the MAC can be obtained according to conventional techniques, e.g. by dispersing the relevant components forming the MAC in an aqueous carrier and optionally washing the obtained suspension in order to remove the excess material.

Said second component is a nanocomponent, i.e. its relative dimension is of about 100 nm or lower, preferably of about 80 nm or lower and more preferably of about 50 nm or lower. The dimensions of the MAC, in particular its mean diameter in number, can be determined according to conventional techniques, such as, for instance, photon correlation spectroscopy. For instance, a ZetaSizer 3000 Has (Malvern Instruments Gmbh) can be used. Particularly when the MAC incorporates a desired targeting ligand, bioactive agent and/or diagnostic agent within its structure, its dimensions are preferably of at least 0.1 nm, more preferably of at least 1 nm.

Preferably, the MAC has a mean dimension which is at least 10 times less or smaller than the mean dimension of the microvesicles to which the MAC is associated, more preferably at least 50 times less or smaller. Said mean dimension is in general not lower than 1000 times, preferably not lower than 500 times.

As it can be appreciated, because of the relatively smaller dimensions of the MAC with respect to the gas-filled microvesicle, it is possible to associate a relatively large amount of MACs to the microvesicles, thus increasing the effectiveness of the assembly in terms of a higher number of binding targeting moieties and/or of the amount of releasable therapeutic or diagnostic agent incorporated therein. In addition, said relatively small dimensions of the MAC allow to obtain assemblies with dimensions comparable to the dimensions of the microvesicles. It is in fact preferred that the mean diameter in number of an assembly according to the invention is not higher than about 30% the mean diameter of the microvesicle measured before the assembling, more preferably not higher than 20% and much more preferably not higher than 10%.

In some embodiments of the invention, the charged material may form the substantial totality of the MAC, i.e. 90% by mole or more. In some other embodiments, it is preferable that the charged molecules forming the structure of said MAC do not represent the totality of the compounds forming said structure, thus being admixed with a certain amount of neutral compounds. Said charged molecules may thus represent less than about 90% by mole of the total amount of the material forming said MAC. On the other hand, the Applicant has observed that the amount of charged molecules in the MAC should preferably be of at least 0.5% by mole with respect to the total amount of material forming said envelope, in order to allow an effective interaction with the charged microvesicle. Preferably, said amount is of at least 1%, more preferably of at least 2% by mole. In some preferred embodiments of the invention, the amount of charged molecules forming the structure of the MAC is preferably of about 50% or lower, more preferably of about 20% or lower.

Micelles

As previously mentioned, a preferred component to be associated with a microvesicle in an assembly of the invention is a micelle. The term "micelle" as used herein includes both micelles and mixed micelles, where the term mixed micelles refers to a micellar structure formed by a mixture of two or more different compounds, at least one of which is an amphiphilic compound capable of forming a micellar structure. The term mixed micelles thus includes within its meaning also micelles formed by at least one compound, preferably an amphiphilic compound, which is in general unable to form a micellar structure when dispersed as such in an aqueous carrier, but which is capable of forming said structure when used in combination with suitable amounts of a micelle-forming amphiphilic compound. Examples of mixed micelles are micelles formed by unmodified phospholipids (which are in general not capable of forming micelles when dispersed as the sole material in an aqueous carrier) and by a micelle-forming compound (e.g. PEG-modified phospholipid or a fatty acid salt). As know in the art, micelles are formed by amphiphilic molecules dispersed in water when the concentration of these molecules exceeds a predetermined value known as CMC (critical micellar concentration). At concentrations below the CMC, the molecules are in general dispersed in the aqueous solution as single molecules. Above the CMC, the amphiphilic molecules tend to organize in supermolecular structures, in equilibrium with the free molecules in the solution, said structures being characterized by the fact that the hydrophobic (lipid) tail of the molecule is disposed towards the inner portion of the structure while the hydrophilic (polar or ionic) headgroup of the molecule is disposed on the outer portion of the structure. The CMC of an amphiphilic molecule can be determined experimentally using techniques standard in the art. For example, the CMC of a surfactant can be determined by plotting a property as a function of the concentration of the surfactant. The property usually varies linearly with the increase of surfactant concentration up to the CMC, and after this concentration, the curve (or the property) becomes non-linear. Suitable properties which can be used for the determination of the CMC include refractive index, light scattering, surface tension, electric conductivity, osmotic pressure and the like. For the purpose of the invention, preferred micelle-forming materials are those having a relatively low CMC, e.g. of about 10 mM or lower.

Micelles have typically a dimension comprised from about 0.1 nm to about 100 nm, preferably from about 1 nm to about 50 nm. The mean diameter in number ($D_N$) is of about 50 nm or less, preferably of about 20 nm or less and much more preferably of 10 nm or less, down to e.g. 1 nm, preferably about 2 nm.

A review of micelles, micellar systems and methods of preparation thereof can be found, for instance, in the reference book: "Surfactants and Polymers in Drug Delivery", by M. Malmsten, Ch. 2, pp. 19-50, Marcel Dekker Inc. Ed., 2002).

Suitable materials useful for forming micelles to be associated with microvesicles in an assembly of the invention can be selected among the lipids and phospholipids material previously listed.

Examples of micelle-forming compounds are PEG-modified phospholipids, including in particular PEG-modified phosphatidylethanolamines such as DMPE-PEG2000, DMPE-PEG3000, DMPE-PEG4000, DPPE-PEG5000, DPPE-PEG2000, DPPE-PEG3000, DPPE-PEG4000, DPPE-PEG5000, DSPE-PEG2000, DSPE-PEG3000, DSPE-PEG4000, DSPE-PEG5000, DAPE-PEG2000, DAPE-PEG3000, DAPE-PEG4000 or DAPE-PEG5000; alkylammonium salts comprising at least one ($C_{10}$-$C_{20}$), preferably ($C_{14}$-$C_{18}$), alkyl chain, such as, for instance stearylammonium chloride, hexadecylammonium chloride, dimethyldioctadecylammonium bromide (DDAB), hexadecyltrimethylammonium bromide (CTAB); tertiary or quaternary ammonium salts comprising one or preferably two ($C_{10}$-$C_{20}$), preferably ($C_{14}$-$C_{18}$), acyl chain linked to the N-atom through a ($C_3$-$C_6$) alkylene bridge, such as 1,2-distearoyl-3-trimethylammonium-propane (DSTAP), 1,2-dipalmitoyl-3-trimethylammonium-propane (DPTAP), 1,2-dioleoyl-3-trimethylammonium-propane (DOTAP), 1,2-distearoyl-3-dimethylammonium-propane (DSDAP); fatty acid salts, preferably alkali, in particular sodium salts, such as sodium palmitate, sodium stearate, sodium oleate, sodium linoleate, sodium dodecanoate, 1,2-dipalmitoyl-sn-3-succinylglycerate sodium salt or 1,3-dipalmitoyl-2-succinylglycerol sodium salt.

Polymers including hydrophobic and hydrophilic portions therein (also known as "polymeric surfactants") can also be used to prepare micellar suspensions. Examples of suitable polymeric surfactants include, without limitation, polyethyleneoxides (PEO), such as $(C_8-C_{16})_n$-alkyl PEO monoether, $(C_8-C_{10})_n$-alkyl phenyl PEO, tetramethylbutylphenyl PEO, PEO polysorbates, these PEO being sold under commercial names of Brij®, Lubrol®, Triton®, Nonidet® or Tween®; block copolymers such as ethyleneoxide/propyleneoxide block copolymers (e.g. Pluronic® or Synperonic®), having preferably a MW of from about 3000 to 20000 daltons, preferably of from 5000 to 15000 daltons; sugar derivatives such as $(C_6-C_{10})$alkyl-β-D-glucopyranoside, $(C_8-C_{12})$alkyl-β-D-maltoside; $(C_8-C_{16})$alkyldimethylammoniumpropane-sulfonate; and bile acids and derivatives thereof, such as sodium cholate or sodium deoxycholate.

Additional lipids which can be used for preparing a micelle to be included in an assembly of the invention include, for instance, unmodified phospholipids, such as the previously mentioned fatty acids di-esters of phosphatidylcholine, ethylphosphatidylcholine, phosphatidylglycerol, phosphatidic acid, phosphatidylethanolamine, phosphatidylserine or sphingomyelin. As these unmodified phospholipids are in general unable to form micellar structures when dispersed in an aqueous carrier (as these compounds tends rather to associate as liposomes when dispersed in an aqueous solution), said unmodified phospholipids are preferably used in admixture with any of the previously mentioned micelle-forming compounds. In particular, their amount shall preferably be less than about 80%, more preferably of about 70% or less of the total weight of the mixture of compounds forming the micellar structure. According to a preferred embodiment the micellar component is formed from a mixture comprising from about 30% to 70%, preferably form about 40% to 60% by weight of unmodified phospholipids. The remainder of the mixture can be any of the above listed micelle-forming surfactants.

The desired overall net charge is conferred to the micelle by any of the previously listed negatively or positively charged compounds, in particular lipids or phospholipids, including modified phospholipids.

Thus, examples of phospholipids suitable for conferring an overall negative charge to the micelle are phosphatidylserine derivatives, such as DMPS, DPPS, DSPS; phosphatidic acid derivatives, such as DMPA, DPPA, DSPA; phosphatidylglycerol derivatives such as DMPG, DPPG and DSPG. Also modified phospholipids, in particular PEG-modified phosphatidylethanolamines, can advantageously be employed, such as, for instance DMPE-PEG750, -PEG1000, -PEG2000, -PEG3000 or -PEG5000; DPPE-PEG750, -PEG1000, -PEG2000, PEG3000 or PEG5000; DSPE-PEG750, -PEG1000, -PEG2000, PEG3000 or PEG5000; DAPE-PEG750, -PEG1000, -PEG2000, PEG3000 or PEG5000; and the respective lyso-form of the above cited phospholipids, such as lysophosphatidylserine derivatives, lysophosphatidic acid derivatives (e.g. lyso-DMPA, -DPPA or -DSPA) and lysophosphatidylglycerol derivatives (e.g. lyso-DMPG, -DPPG or -DSPG). Examples of negatively charged lipids are bile acid salts such as cholic acid salts, deoxycholic acid salts or glycocholic acid salts; and fatty acid salts such as palmitic acid salt, stearic acid salt, 1,2-dipalmitoyl-sn-3-succinylglycerol salt or 1,3-dipalmitoyl-2-succinylglycerol salt.

Preferably, the negatively charged compound is selected among DPPA, DPPS, DSPG, DSPE-PEG2000, DSPE-PEG5000 or mixtures thereof.

The negatively charged component is typically associated with a corresponding positive counter-ion, which can be mono- (e.g. an alkali metal), di- (e.g. an earth-alkali metal) or tri-valent (e.g. aluminium). Preferably the counter-ion is selected among alkali metal cations, such as $Li^+$, $Na^+$, or $K^+$, more preferably $Na^+$.

Examples of phospholipids suitable for conferring an overall positive charge to the micelle are esters of phosphatidylcholines, such as 1,2-Distearoyl-sn-glycero-3-Ethylphosphocholine (Ethyl-DSPC), 1,2-Dipalmitoyl-sn-glycero-3-Ethylphosphocholine (Ethyl-DPPC). The negative counterion is preferably an halogen ion, in particular chlorine or bromine. Examples of positively charged lipids are alkylammonium salts, comprising at least one $(C_{10}-C_{20})$, preferably $(C_{14}-C_{18})$, alkyl chain, or tertiary or quaternary ammonium comprising one or preferably two $(C_{10}-C_{20})$, preferably $(C_{14}-C_{18})$, acyl chain linked to the N-atom through a $(C_3-C_6)$ alkylene bridge, such as those previously listed.

Ethyl-DPPC, Ethyl-DSPC, DSTAP or mixtures thereof are preferably employed as positively charged compounds.

The positively charged component is typically associated with a corresponding positive counter-ion, which can be mono- (e.g. halogen), di- (e.g. sulphate) or tri-valent (e.g. phosphate). Preferably the counter-ion is selected among halogen ions, such as $F^-$ (fluorine), $Cl^-$ (chlorine) or $Br^-$ (bromine).

Furthermore, ionic polymers such as those previously listed among the microballoons-forming materials can advantageously be used to form a micelle having an overall (negative or positive) net charge.

As above, the charged molecules can, in some embodiments, advantageously be admixed with a neutral amphiphilic compound, such as those previously listed (including neutral phospholipids), to form the desired micellar structure. Preferred neutral compounds to be admixed with the above listed charged compounds are polymeric surfactants, such as ethyleneoxide-propylenoxide block copolymers, e.g. Pluronic F68, Pluronic F108, Pluronic F-127 (Sigma Aldrich, Missouri, USA); Polyoxyethylated alkyl ether such as Brij® 78 (Sigma Aldrich, Missouri, USA); Polyoxyethylene fatty acid ester such as Myrj® 53 or Myrj® 59 (Sigma Aldrich, Missouri, USA); Polyoxyethylenesorbitan fatty acid ester such as Tween® 60 (Sigma Aldrich, Missouri, USA); Polyethylene glycol tert-octylphenyl ether such as Triton®X-100 (Sigma Aldrich, Missouri, USA); sodium dodecyl sulfate (SDS). According to one embodiment of the invention, the micelles are formed by mixtures of a charged amphiphilic compound with a neutral phospholipid and one or more of the above listed neutral compounds.

In some preferred embodiments of the invention, the amount of charged surfactant can form the substantial totality of the micelle (i.e. at least 80%, preferably at least 90% and more preferably about 100% of the total weight of micelle forming material). In some other preferred embodiments, in particular when at least one compound forming the micelle is an unmodified phospholipid, the total amount of charged surfactant forming the micelle is preferably from about 1% to 80%, more preferably from about 2% to about 50%.

Micelles can be prepared as known in the art by dispersing the above compounds in an aqueous liquid carrier and optionally agitating the mixture. Examples of suitable liquid carriers are water, saline solution (sodium chloride 0.9%), Phosphate buffered saline (10 mM, pH 7.4), HEPES buffer (20 mM, pH 7.4), Glucose 5% w/w in water. For instance, the above compounds can be dispersed in a concentration of from about 1 to 100 mg/ml in an aqueous liquid and dissolved by means of agitation or sonication.

The micelles can then be stored as an aqueous dispersion (e.g. in the aqueous carrier used for their preparation) before being admixed with a suspension containing microvesicles or (as explained in detail in the following of the specification) to an aqueous-organic emulsion from which microvesicles are prepared. Alternatively, the micelle suspension can be freeze-dried according to conventional techniques, to eliminate the liquid and store the final dry product for the subsequent uses.

Liposomes

Another supermolecular structure which can be associated as a MAC to a microvesicle in an assembly according to the invention is a liposome, in particular small unilamellar vesicle (SUV) liposomes.

The term liposome includes substantially spherical aggregations of amphiphilic compounds, including lipid compounds, typically in the form of one or more concentric layers. Typically they are formed in aqueous suspensions and contain at least one bilayer of an amphiphilic compound. The hydrophilic heads of the amphiphilic compounds forming the external layer of the bilayer are directed towards the exterior of the spherical structure, while the hydrophilic heads of the amphiphilic compounds forming the internal layer of the bilayer are directed towards the interior of said spherical structure. The interior of the spherical structure of the liposomes is in general filled with the same liquid of the aqueous suspension, optionally containing additional compounds which are not present (or are present to a lesser extent) in the outer aqueous suspension.

Preferred materials for preparing liposomes are phospholipids, such as those previously listed, optionally in admixture with any of the other previously listed amphiphilic compounds.

SUV liposomes can be formed according to conventional techniques, e.g. by suitably processing MLV (Multilamellar large vesicles) suspensions, for instance by ultrasonication, extrusion or microfluidisation. MLV can be obtained, for instance, by dissolving phospholipids in an organic solvent, evaporating the organic solvent under vacuum to obtain a phospholipid film and finally hydrating the film at a temperature above phospholipid transition temperature. The obtained MLV may thus be exposed to ultrasonic radiations to obtain the desired SUV liposomes. Alternatively, the MLV can be extruded through a plurality of membranes (e.g. of polycarbonate) with decreasing pore size (e.g. 1.0, 0.8, 0.6, 0.4, and 0.2 µm) and then through an extruder with smaller pore dimensions (for example LIPEX Biomembranes®, Canada) to obtain the final SUV. As a further alternative preparation process of SUV, MLV can be homogenised under high pressure in a microfluidizer (e.g. from Microfluidics Corporation), to reduce the liposome size to approximately 100 nm or less, depending on the amount of recirculation of the liposomes in the microfluidizer. These and other preparation methods of SUV are disclosed, for instance, in the reference book "Liposomes, a practical approach", edited by Roger R. C. New, Oxford University Press, 1989.

Dimensions of SUV liposomes are typically from about 25 nm to about 100 nm, preferably from about 30 nm to about 100 nm. The mean diameter in number can vary from about 30 nm to about 60 nm, preferably from about 30 to about 50 nm.

A review of liposomes and their preparation methods is also given in the above cited reference book "Surfactants and Polymers in Drug Delivery", by M. Malmsten, Ch. 4, pp. 87-131, Marcel Dekker Inc. Ed., 2002).

Other structures which can be associated as a MAC to a microvesicle in an assembly of the invention include colloidal nanoparticles, e.g. colloidal gold nanoparticles. These nanoparticles are typically obtained by adding a suitable dispersing agent to an aqueous solution comprising substantially insoluble solid nanoparticles, thus forming an aqueous suspension of colloidal nanoparticles (i.e. solid nanoparticles coated with the dispersing agent). For instance, colloidal gold nanoparticles can be obtained by dispersing gold nanoparticles (with a diameter of from about 2 to 50 nm) with sodium citrate in an aqueous solution (see e.g. Grabar, "Preparation and Characterization of Au colloid monolayers", Analytical Chemistry, vol. 67, p. 735,1995). Colloidal gold nano-particles associated with gas-filled microvesicles can be used to increase penetration depth in a selected tissue when said microvesicles are caused to disintegrate (e.g. induced by controlled high energy ultrasound irradiation). Thus, an assembly comprising colloidal gold nanoparticles can be for instance associated with a further MAC comprising a bioactive agent, in order to increase the penetration depth of said bioactive agent into the selected tissue, thus enhancing the effectiveness of the therapeutic treatment.

Further MACs can be formed by solid polymeric nanoparticles. These solid polymeric nanoparticles can be formed by any of the polymeric materials previously listed in connection with the preparation of gas-filled microballoons, thus including biodegradable physiologically acceptable polymers, such as substantially water insoluble polysaccharides (e.g. chitosan or chitin), polycyanoacrylates, polylactides and polyglycolides and their copolymers, copolymers of lactides and lactones such as γ-caprolactone or δ-valerolactone, copolymers of ethyleneoxide and lactides, polyethyleneimines, polypeptides, and proteins such as gelatin, collagen, globulins or albumins. Other suitable polymers are those mentioned in the above cited U.S. Pat. No. 5,711,933 and previously listed. Non-biodegradable polymers in particular water-insoluble, physiologically acceptable and bioresistant polymers, can also be used, preferably in admixture with any of the above biodegradable polymer. Said polymer can be, for instance, a polyolefin, such as polystyrene, an acrylic resin such as polyacrylates of polyacrylonitrile, a polyester, such as polycarbonate, polyurethane, polyurea and their copolymers. ABS (acryl-butadiene-styrene) is a preferred copolymer.

Targeting Ligands and Bioactive/Diagnostic Agents

The MAC, in particular in the form of micelles, of an assembly according to the invention, may advantageously include within its structure compounds having a targeting, diagnostic and/or biological activity.

The targeting ligand included in the MAC may be synthetic, semi-synthetic, or naturally-occurring. Materials or substances which may serve as targeting ligands include, for example, but are not limited to proteins, including antibodies, antibody fragments, receptor molecules, receptor binding molecules, glycoproteins and lectins; peptides, including oligopeptides and polypeptides; peptidomimetics; saccharides, including mono and polysaccharides; vitamins; steroids, steroid analogs, hormones, cofactors, bioactive agents and genetic material, including nucleosides, nucleotides and polynucleotides.

Examples of suitable targets and targeting ligands are disclosed, for instance, in U.S. Pat. No. 6,139,819, which is herein incorporated by reference.

The targeting ligand can be a compound per se which is admixed with the other components of the MAC composition to be included in the final structure of the MAC or can be a compound which is bound to an amphiphilic molecule employed for the formation of the MAC.

In one preferred embodiment, the targeting ligand can be bound to an amphiphilic molecule of the MAC through a covalent bond. In such a case, the specific reactive moiety that needs to be present on the amphiphilic molecule will depend on the particular targeting ligand to be coupled thereto. As an example, if the targeting ligand can be linked to the amphiphilic molecule through an amino group, suitable reactive moieties for the amphiphilic molecule may be isothiocyanate groups (that will form a thiourea bond), reactive esters (to form an amide bond), aldehyde groups (for the formation of an imine bond to be reduced to an alkylamine bond), etc.; if the targeting ligand can be linked to the amphiphilic molecule through a thiol group, suitable complementary reactive moieties for the amphiphilic molecule include haloacetyl derivatives or maleimides (to form a thioether bond); and if the targeting ligand can be linked to the amphiphilic molecule through a carboxylic group, suitable reactive moieties for the amphiphilic molecule might be amines and hydrazides (to form amide or alkylamide bonds). In order to covalently bind a desired targeting ligand, at least part of the amphiphilic compound forming the MAC shall thus contain a suitable reactive moiety and the targeting ligand containing the complementary functionality will be linked thereto according to known techniques, e.g. by adding it to an aqueous dispersion comprising the amphiphilic components of the MAC. The amphiphilic compound can be combined with the desired targeting ligand before preparing the MAC, and the so obtained combination can be used in the preparation process of the MAC. Alternatively, the targeting ligand can be linked to the respective amphiphilic compound during the preparation process of the MAC or can be directly linked to the amphiphilic compound already in a micellar structure.

According to an alternative embodiment, the targeting ligand may also be suitably associated to the MAC via physical and/or electrostatic interaction. As an example, a functional moiety having a high affinity and selectivity for a complementary moiety can be introduced into the amphiphilic molecule, while the complementary moiety will be linked to the targeting ligand. For instance, an avidin (or streptavidin) moiety (having high affinity for biotin) can be covalently linked to a phospholipid while the complementary biotin moiety can be incorporated into a suitable targeting ligand, e.g. a peptide or an antibody. The biotin-labelled targeting ligand will thus be associated to the avidin-labelled phospholipid of the MAC by means of the avidin-biotin coupling system. Alternatively, both the phospholipid and the targeting ligand can be provided with a biotin moiety and subsequently coupled to each other by means of avidin (which is a bifunctional component capable of bridging the two biotin moieties). Examples of biotin/avidin coupling of phospholipids and peptides are also disclosed in the above cited U.S. Pat. No. 6,139,819. Alternatively, van der Waal's interactions, electrostatic interactions and other association processes may associate or bind the targeting ligand to the amphiphilic molecules.

According to an alternative embodiment, the targeting ligand can be a compound which is admixed with the components forming the MAC, to be eventually incorporated the MAC structure, such as, for instance, a lipopeptide as disclosed e.g. in International patent Applications WO 98/18501 or 99/55383, both herein incorporated by reference.

Alternatively, a MAC can first be manufactured, which comprises a compound having a suitable moiety capable of interacting with a corresponding complementary moiety of a targeting ligand; thereafter, the desired targeting ligand is added to the MAC suspension, to bind to the corresponding complementary moiety on the MAC. As an additional alternative, an assembly can be prepared, which comprises a MAC including a compound having a suitable moiety capable of interacting with a corresponding complementary moiety of a targeting ligand; thereafter, the desired targeting ligand is added to the assembly suspension, to bind to the corresponding moiety on the MAC.

Examples of suitable specific targets to which the assembly can be directed are, for instance, fibrin and the GPIIbIIIa binding receptor on activated platelets. Fibrin and platelets are in fact generally present in "thrombi", i.e. coagula which may form in the blood stream and cause a vascular obstruction. Suitable binding peptides are disclosed, for instance, in the above cited U.S. Pat. No. 6,139,819. Further binding peptides specific for fibrin-targeting are disclosed, for instance, in International patent application WO 02/055544, which is herein incorporated by reference.

Other examples of important targets include receptors in vulnerable plaques and tumor specific receptors, such as kinase domain region (KDR) and VEGF (vascular endothelial growth factor)/KDR complex. Binding peptides suitable for KDR or VEGF/KDR complex are disclosed, for instance, in International Patent application WO 03/74005 and WO 03/084574, both herein incorporated by reference.

Bioactive agents include any compound or material capable of being used in the treatment (including diagnosis, prevention, alleviation, pain relief or cure) of any pathological status in a patient (including malady, affliction, disease lesion or injury). Examples of bioactive agents are those previously listed. Among these, drugs or pharmaceuticals are preferred, in particular those drugs consisting of an organic molecule (typically a synthetic molecule) which is substantially hydrophobic or which contain a relevant portion thereof which is substantially hydrophobic. These molecules may in fact be incorporated relatively easily in the structure of a MAC, in particular of a micelle, because of their affinity with the lipophilic (or hydrophobic) portion of the amphiphilic material forming the MAC. For instance, the organic molecule can be dispersed in the aqueous carrier containing the amphiphilic material forming the MAC, in particular the micelle, where it will be incorporated by affinity into the hydrophobic portion of the MAC. Alternatively, also hydrophilic drugs or organic molecules can be incorporated into the MAC, in particular when this latter is in the form of a liposome. In this case, said hydrophilic compound will preferably be contained in the internal aqueous portion of the liposome.

Examples of drugs which can be incorporated into or associated to the MAC's structure are, for instance those mentioned in the above cited WO 99/53963, thus including antineoplastic agents such as vincristine, vinblastine, vindesine, busulfan, chlorambucil, spiroplatin, cisplatin, carboplatin, methotrexate, adriamycin, mitomycin, bleomycin, cytosine arabinoside, arabinosyl adenine, mercaptopurine, mitotane, procarbazine, dactinomycin (antinomycin D), daunorubicin, doxorubicin hydrochloride, taxol, plicamycin, aminoglutethimide, estramustine, flutamide, leuprolide, megestrol acetate, tamoxifen, testolactone, trilostane, amsacrine (m-AMSA), asparaginase (Lasparaginase), etoposide, interferon a-2a and 2b, blood products such as hematoporphyrins or derivatives of the foregoing; biological response modifiers such as muramylpeptides; antifungal agents such as ketoconazole, nystatin, griseofulvin, flucytosine, miconazole or amphotericin B; hormones or hormone analogues such as growth hormone, melanocyte stimulating hormone, estradiol, beclomethasone dipropionate, betamethasone, cortisone acetate, dexamethasone, flunisolide, hydrocortisone, methylprednisolone, paramethasone acetate, prednisolone, prednisone, triamcinolone or fludrocortisone acetate; vitamins such as cyanocobalamin or retinoids; enzymes such as alkaline phosphatase or manganese superoxide dismutase; antiallergic agents such as amelexanox; anticoagulation agents such as warfarin, phenprocoumon or heparin; antithrombotic agents; circulatory drugs such as propranolol; metabolic potentiators such as glutathione; antitubercular such as p-aminosalicylic acid, isoniazid, capreomycin sulfate, cyclosexine, ethambutol, ethionamide, pyrazinamide, rifampin or streptomycin sulphate; antivirals such as acyclovir, amantadine, azidothymidine, ribavirin or vidarabine; blood vessel dilating agents such as diltiazem, nifedipine, verapamil, erythritol tetranitrate, isosorbide dinitrate, nitroglycerin or pentaerythritol tetranitrate; antibiotics such as dapsone, chloramphenicol, neomycin, cefaclor, cefadroxil, cephalexin, cephradine, erythromycin, clindamycin, lincomycin, amoxicillin, ampicillin, bacampicillin, carbenicillin, dicloxacillin, cyclacillin, picloxacillin, hetacillin, methicillin, nafcillin, penicillin or tetracycline; antiinflammatories such as diflunisal, ibuprofen, indomethacin, meclefenamate, mefenamic acid, naproxen, phenylbutazone, piroxicam, tolmetin, aspirin or salicylates; antiprotozoans such as chloroquine, metronidazole, quinine or meglumine antimonate; antirheumatics such as penicillamine; narcotics such as paregoric; opiates such as codeine, morphine or opium; cardiac glycosides such as deslaneside, digitoxin, digoxin, digitalin or digitalis; neuromuscular blockers such as atracurium mesylate, gallamine triethiodide, hexafluorenium bromide, metocurine iodide, pancuronium bromide, succinylcholine chloride, tubocurarine chloride or vecuronium bromide; sedatives such as amobarbital, amobarbital sodium, apropbarbital, butabarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, secobarbital sodium, talbutal, temazepam or triazolam; local anaesthetics such as bupivacaine, chloroprocaine, etidocaine, lidocaine, mepivacaine, procaine or tetracaine; general anaesthetics such as droperidol, etomidate, fentanyl citrate with droperidol, ketamine hydrochloride, methohexital sodium or thiopental and pharmaceutically acceptable salts (e.g. acid addition salts such as the hydrochloride or hydrobromide or base salts such as sodium, calcium or magnesium salts) or derivatives (e.g. acetates) thereof; and radiochemicals, e.g. comprising alpha-, beta-, or gamma-emitters such as, for instance $^{177}$Lu, $^{90}$Y or $^{131}$I. Of particular importance are antithrombotic agents such as heparin and agents with heparin-like activity such as antithrombin III, dalteparin and enoxaparin; blood platelet aggregation inhibitors such as ticlopidine, aspirin, dipyridamole, iloprost and abciximab; and thrombolytic enzymes such as streptokinase and plasminogen activator. Other examples of bioactive agent include genetic material such as nucleic acids, RNA, and DNA of natural or synthetic origin, including recombinant RNA and DNA. As mentioned in the above patent, DNA encoding certain proteins may be used in the treatment of many different types of diseases. For example, tumour necrosis factor or interleukin-2 may be provided to treat advanced cancers; thymidine kinase may be provided to treat ovarian cancer or brain tumors; interleukin-2 may be provided to treat neuroblastoma, malignant melanoma or kidney cancer; and interleukin-4 may be provided to treat cancer.

Diagnostic agents which may be incorporated into or associated to the MAC in an assembly of the invention are any compound, composition or particle which may allow imaging enhancement in connection with diagnostic techniques, including, magnetic resonance imaging, X-ray, in particular computed tomography, optical imaging, nuclear imaging or molecular imaging. Examples of suitable diagnostic agents are, for instance, magnetite nanoparticles, iodinated compounds, such as Iomeprol®, or paramagnetic ion complexes, such as hydrophobic gadolinium complexes. For instance, magnetite nanoparticles can be admixed with a negatively charged amphiphilic material (and optionally a neutral one), such as those previously mentioned, in order to stabilize said particles and keep them dispersed in an aqueous solution. U.S. Pat. No. 5,545,395, herein incorporated by reference, gives some examples of preparation of said stabilized magnetite particles, e.g. by using a mixture of DPPA and Pluronic® for stabilizing said particles. Alternatively, gadolinium complexes can be admixed with suitable micelle-forming compounds, for instance as disclosed in European Patent EP 804 251 (herein incorporated by reference), to form a gadolinium containing MAC.

The Assembly

In order to evaluate the relative compositions of the assemblies of the invention, the Applicant has found it useful to refer to the amounts of charged compounds in the microvesicles and in the MAC (expressed as "equivalents of charge") and to the ζ-potential of the suspensions of microvesicles and assemblies.

The term "equivalent of charge" (EC), indicates the number of charges per mole of said compound. Thus, one mole of a mono-ionic compound contains one EC, one mole of a di-ionic compound contains two EC and so on.

The ζ-potential (zeta-potential), also called electrokinetic potential, is the electric potential at the surface of a colloidal particle relative to the potential in the bulk medium at a long distance. It can be measured according to conventional micro-electrophoresis analytical methods, e.g. via the determination of the velocity of the particles in a driving electric field by Laser-Doppler-Anemometry. For example, the Zeta-Sizer 3000 Has (Malvern Instrument GmbH) can be advantageously used. In the practice, the ζ-potential of the initial suspension of microvesicles is first determined, which can have a positive or negative value, depending whether the microvesicles contain positively or negatively charged compounds, respectively. Then, the ζ-potential is measured on the final suspension containing the assembly (i.e. after the necessary washing steps for removing possibly unbound MACs). In general, the addition of MACs of opposite sign with respect to the microvesicles determines a more or less pronounced decrease in absolute value of the ζ-potential of the suspension. In particular, suspensions comprising positively charged microvesicles will show a decrease of the ζ-potential upon addition of a suspension of negatively charged MACs, while suspensions comprising negatively charged microvesicles will show a relative increase of the ζ-potential (i.e. a decrease in absolute value) upon addition of a suspension of positively charged MACs. As observed by the Applicant, preferred assemblies are those suspensions showing a substantial decrease in absolute value with respect to the ζ-potential of the initial microvesicles suspension, i.e. a decrease of at least 50%, preferably of at least 75% and more preferably of at least 90% of said initial value. Particularly preferred assemblies' suspensions are those showing a substantially neutral ζ-potential (i.e. 0±10 mV, corresponding to an absolute decrease of about 100% with respect to the initial potential of the microvesicles suspension) or a ζ-potential opposite in sign with respect to the ζ-potential of the initial microvesicles' suspension. As observed by the Applicant, when the ζ-potential of the assembly suspension remains equal in sign with an absolute decrease of less than 50% with respect to the ζ-potential of the initial microvesicles suspensions, this may be an indication that an insufficient number of MACs are associated to the microvesicles.

According to a preferred embodiment, the amount of charged MACs in the assembly is such as to confer a substantially neutral ζ-potential to said assembly or a ζ-potential which is opposite in sign with respect to the ζ-potential of the microvesicle. As observed by the Applicant, to obtain said neutral or opposite in sign ζ-potential of the assembly it is however not necessary that the assembly contains an excess of equivalents of charge from the MAC. As a matter of fact, it has been observed that assemblies composed of positive microvesicles and negative MACs and having a ratio between EC in the MAC and equivalents of opposite charge in the microvesicle of about 1:5 (i.e. an excess of about 5 times of positive charges on the microvesicles) may nevertheless show a substantially neutral or negative ζ-potential. Although not wishing to be bound to any particular theory, it may be supposed that the (negative) charges comprised in the MACs are disposed on the outer surface of the assembly; if the number of MACs associated to the microvesicle is sufficiently high, the excess of (positive) opposite charges on the microvesicle may result, at least partially, screened by said MACs. Thus, as the ζ-potential measured on a particle is strongly influenced by the charges present on the outer boundary of said particle, even an assembly having an excess of (positive) equivalents of charge deriving from a microvesicle may show a negative ζ-potential, if the amount of (negatively) charged MACs is sufficient to partially screen the (positive) charges of the microvesicle. All the above is of course also applicable to assemblies formed by negatively charged microvesicles and positively charged MACs.

In general, the ratio between the EC on the microvesicles and the EC of charge on the MAC in the final suspension of the assembly can vary from about 10:1 to about 1:10. According to a preferred embodiment, the microvesicle/MAC EC ratio in the formed assembly is preferably of about 3:1 or less, more preferably of about 2:1 or less and much more preferably of about 3:2 or less. Depending from the amount of charged compounds forming the microvesicles and the MACs, said ratio can of course be lower, for instance of about 1:1 and down to e.g. about 1:4 or less.

In view of the relatively small dimensions of the MAC, the dimensions (mean diameter in number) of the assembly are typically of about 10 μm or lower and in general of about 1 μm or more. Preferred dimension of an assembly according to the invention are from about 1 μm to about 8 μm, more preferably from about 2 μm to about 5 μm.

According to a further embodiment of the invention, multi-layer assemblies can be formed by associating a gas-filled microvesicle to a plurality of layers of components, having an alternate charge. Thus, for instance, it is possible to associate to a negatively charged microvesicle a first layer of components (e.g. micelles) having a positive charge; then a second layer of components (e.g. again micelles or liposomes) having a negative charge can be associated to this assembly, and so on. Whilst the association of the first layer of components to the microvesicles will cause a reduction in absolute value of the ζ-potential (with respect to the one measured on a suspension of the sole microvesicles), the further association of a second layer of components (having an opposite charge with respect to the first component) will cause the ζ-potential to change again towards values closer to those of the suspension of sole microvesicles.

According to a first method of preparation, the assembly can be obtained by admixing an aqueous suspension comprising the microvesicles (obtained according to any of the above cited manufacturing methods) with an aqueous suspension comprising the second component of the assembly (obtained according to any of the above cited manufacturing methods).

Optionally, the so obtained mixture can be subjected to one or more washing steps, in order to remove the excess of non-associated components. The washing can be performed with any conventional washing technique, by using suitable washing solutions, such as distilled water, phosphate buffered saline, Tris/glycerol buffer, saline or 5% glucose solution. The phase of the washed mixture comprising the assembly of the invention (in general the supernatant phase) is thus separated and collected; optionally, the recovered assembly-containing suspension is finally diluted before use, e.g. with any of the above cited physiologically acceptable carrier.

Upon formation, the suspension comprising the assembly of the invention can be stored for a subsequent administration or can be directly administered. If desired, the liquid carrier of the suspension can be eliminated (e.g. by freeze-drying) to obtain a dry powder of the assembly which can be stored (preferably in the presence of a gas suitable for forming the gas-filled microvesicles upon reconstitution) for relatively long periods of time before reconstitution.

Alternatively, the two components of the assembly can be stored as separate compositions in dried form (e.g. freeze dried) and reconstituted as a suspension before administration. For the storage, the dried components are preferably kept in an atmosphere of the gas which will form the microvesicles upon reconstitution with water. The reconstitution with an aqueous liquid carrier may take place separately on the two dried compositions comprising the respective components of the assembly, thus obtaining two separate suspensions which are subsequently admixed to obtain the desired assembly suspension. Alternatively, the two dried compositions may be admixed together and then reconstituted as a single suspension with an aqueous liquid carrier. In this latter case, the mixed components of the assembly are stored in the presence of the gas which will form the microvesicles upon reconstitution with the aqueous liquid carrier. According to a preferred embodiment, the dried MAC composition is first reconstituted with a physiologically acceptable aqueous carrier and the obtained suspension is then used for reconstituting the dried microvesicle composition, to finally obtain a suspension of the assembly.

Any of the above preparation methods can also be used for preparing a multi-layer assembly as described above, by first admixing the charged gas filled microvesicles with a first component having an opposite charge and then by admixing the formed assembly with a second component having the same charge as the microvesicles.

For the preparation of the assembly from two separate preparations of microvesicles and MACs, it may be advantageous to add an excess amount of MACs with respect to the relative amount of MACs which is desired in the final assembly, in particular because a certain amount of said MACs can be removed during the optional washing steps of the assemblies' suspension. In general, it is preferred that the amount of EC in the composition employed for the preparation of the MAC is at least substantially equal to the EC in the composition employed for the preparation of the microvesicles (i.e. EC ratio of about 1:1). Preferably said EC ratio is of about 2:1 or higher, more preferably of at least about 3:1 or higher, up to e.g. 30:1.

According to a preferred embodiment, an aqueous suspension of a MAC (in particular of micelles as above defined) is added to an aqueous/organic emulsion comprising a phospholipid and a lyoprotecting agent, prepared according to the method disclosed in the above cited WO 04/069284. In this case, the charged MACs will associate with the opposite charged layer of amphiphilic material surrounding the microdroplets of the emulsion. The MAC is generally added in an amount such that ratio between the equivalents of charge in the MAC and the EC in the microvesicles of the suspension is of at least about 1:2 or higher, preferably 2:3 or higher and much more preferably of at least 1:1 or higher, up to e.g. 10:1. Similarly, an aqueous suspension of MAC can be added to a gas microbubble dispersion which has been obtained by submitting an aqueous medium comprising a phospholipid (and optionally other amphiphilic film-forming compounds and/or additives) to a controlled high agitation energy in the presence of a desired gas, as previously mentioned.

Freeze drying of the mixture provides the desired assembly as a lyophilized powder, which can be stored in contact with the desired gas and subsequently reconstituted as a physiological suspension by addition of an aqueous carrier.

The gas in contact with the stored freeze-dried products (assembly, microvesicles and/or MACs) can be present in the storage container at a substantial atmospheric pressure (i.e. about 1020 mbar+/−5%) or at a pressure lower than the atmospheric one (e.g. 900 mbar or lower) as disclosed in European patent application EP 1228770.

Injectable compositions after reconstitution of the lyophilised contrast agent should be, as far as possible, isotonic with blood. Hence, before injection, small amounts of isotonic agents may also be added to the suspensions comprising the assembly of the invention. The isotonic agents are physiological solutions commonly used in medicine such as, for example, aqueous saline solution (0.9% NaCl), 2.6% glycerol solution or 5% dextrose solution. The reconstitution of the aqueous suspensions is generally obtained by simple dissolution of the gas-stored dried film forming surfactant and gentle agitation.

The volume and concentrations of the reconstitution liquid may desirably be balanced to make the resulting ready-to-use formulations substantially isotonic. Hence the volume and concentration of reconstitution fluid chosen will be dependent on the type and amount of stabilizer (and other bulking agents) present in the freeze-dried product.

As it will be appreciated by those skilled in the art, the assembly according to the invention allows an extreme flexibility in the preparation of different assemblies for different purposes. As a matter of fact, the structure of the basic carrier component employed for the ultrasound diagnostic/therapeutic methods (i.e. the microvesicle) does not need to be subjected to any particular modifications, thus avoiding possible drawbacks in terms of stability of said component. Such component only needs to have an overall net charge on its envelope, which result can be easily obtained by using conventional materials normally used for forming said envelope. As a matter of fact, the electrostatic interaction between the microvesicle and the MAC allows an effective association between the two components, without the need of modifying the structure of the microvesicle. On the other side, the second component of the assembly, the stability of which is much less sensitive to possible modifications of its composition, can be easily adapted to the specific purpose requested to the assembly, by associating the desired targeting ligand and/or bioactive compound to it. Furthermore, due to the relatively small dimensions of the MAC with respect to the microvesicle, it is possible to associate a relatively large number of MACs to each microvesicle, thus increasing the efficiency of the system.

In addition, the microvesicles of the assembly can be easily associated with more than one type of different nano-components, thus resulting in a "multipurpose" assembly. In particular, one single preparation of charged microvesicles (e.g. positively charged) can be used as a carrier to be associated with any desired type of MAC bearing an opposite charge (e.g. negative). Alternatively, a multipurpose assembly can also be obtained by preparing a multilayer assembly as previously described, where the different components of opposite charge are disposed as alternate layers around the microvesicle. The different MAC's associated to the microvesicle can differ in their chemical composition or supermolecular structure (e.g. micelles vs. liposomes), as well as in the targeting ligand, diagnostic agent and/or bioactive agent contained therein; advantageously, a multipurpose assembly will contain a combination of any of these. For instance, the microvesicle component can be combined with a first nano-component (e.g. in micellar form), comprising in its structure at least one targeting ligand (capable to link to a specific receptor associated to a pathologic status or disease), and with a second nano-component (e.g. either in micellar form or as a liposome), comprising either a second targeting ligand or a bioactive compound (e.g. a therapeutic compound for treating said pathologic status or disease). When an assembly comprising a combination of a "targeting ligand bearing component" and of a "bioactive compound bearing component" are employed, particularly when a "multilayer" assembly is prepared, the component bearing the targeting ligand is preferably separately associated as last component to the gas-filled microvesicle, in order to allow an effective targeting activity of the assembly. An example of a multipurpose assembly is, for instance, an assembly comprising a gas filled microvesicle, a first component in micellar form, which comprises a targeting ligand binding to a tumor specific receptor, and a second component comprising a radiochemical (bound to a micelle-forming compound or incorporated into a liposome) for the therapeutic treatment of the tumor.

An assembly of the invention can thus be used for a variety of diagnostic and/or therapeutic methods.

For instance, an assembly comprising a MAC with a suitable targeting ligand can be used to target a specific organ or tissue, which can then be selectively imaged according to conventional ultrasound imaging techniques, because of the enhanced imaging determined by the gas-filled microvesicles bound to said organ or tissue. If a diagnostic agent (e.g. for MRI) is further included in the assembly, use of combined diagnostic techniques is possible. Furthermore, if a bioactive agent is included in the assembly (e.g. included in a liposome), it is possible to provoke an ultrasound-mediated release of said bioactive agent at a selected target (e.g. where a targeting ligand binds) by applying a controlled acoustic power capable of destroying the gas-filled microvesicles, as disclosed for instance in WO 99/39738, herein incorporated by reference.

Of course, an assembly of the invention may also contain, together with components bearing a targeting ligand or a pharmaceutical active agent, also components which are free of said compounds, which are employed, for instance, for balancing the overall charge of the assembly.

As previously mentioned, it has also been observed that the association of a component, in particular of a plurality of micelles, to a gas-filled microvesicle to form an assembly according to the invention, results in an increased resistance of said microvesicles towards pressure. For instance, it has been observed that microvesicles showing a $P_{C50}$ (i.e. a critical pressure at which more than 50% of the microvesicle population is destroyed) of about 500 mm Hg, may increase said value of $P_{C50}$ to at least 600 mm Hg and up to about 800 mm Hg, when associated to different types of micelles to form an assembly of the invention.

Kit

Another aspect of the invention relates to diagnostic kits comprising the assembly of the invention or its respective separate components, optionally further comprising the aqueous liquid carrier.

According to a first embodiment, said kit is a two component kit comprising the assembly of the invention together with an aqueous liquid carrier. Said two component kit can include two separate containers or a dual-chamber container.

In the former case the first container is preferably a conventional septum-sealed vial, wherein the vial containing the assembly as a lyophilized residue (obtained according to any of the above illustrated methods) in contact with the desired gas is sealed with a septum through which the carrier liquid may be injected for reconstituting the suspension of the gas-filled microvesicles/MACs assemblies. The carrier liquid is contained into a second container which preferably takes the form of a syringe. The syringe is preferably re-filled with the reconstituted suspension and used subsequently to administer the contrast agent by injection. Instead of the formed assembly, the first container can alternatively contain mixture of separately freeze-dried MAC and microvesicles compositions, which will form the desired assembly upon reconstitution with the aqueous carrier. Although in general hand shaking of the container provides the desired energy for reconstituting the suspension, means for directing or permitting application of sufficient energy towards the container can be provided (e.g. a Vortex mixer), in order to assure suitable reconstitution of the assemblies' suspension. The dual-chamber container is preferably a dual-chamber syringe, where the components are kept separated e.g. by means of a removable septum, and once the lyophilisate has been reconstituted by gentle shaking, the container can be used directly for injecting the contrast agent. As before, means for directing or permitting application of sufficient energy towards of the container can be provided.

It can be appreciated by one ordinary skilled in the art that other two-chamber reconstitution systems capable of combining the dried powder with the aqueous solution in a sterile manner are also within the scope of the present invention. In such systems, it is particularly advantageous if the aqueous phase can be interposed between the water-insoluble gas and the environment, to increase shelf life of the product.

According to another embodiment, a kit according to the invention is an at least two component kit comprising a MAC composition, a microvesicle composition and, optionally, an aqueous carrier.

These are preferably presented as at least two separate containers, the first one containing the lyophilized microvesicle composition (e.g. in contact with a desired gas) and the second one containing the desired lyophilized MAC composition (optionally in contact with a desired gas or under vacuum). A third optional container, containing the aqueous carrier for reconstitution can advantageously be included in the kit. If desired, additional containers containing further lyophilized MAC compositions can be included in the kit. For administration, the MAC suspension is first reconstituted in the aqueous carrier and the obtained suspension is then used for reconstituting the microvesicle composition, thus forming the desired assembly suspension.

No specific containers vial or connection systems are required; the present invention may use conventional containers, vials and adapters. The only requirement is a good seal between the stopper and the container. The quality of the seal, therefore, becomes a matter of primary concern; any degradation of seal integrity could allow undesirables substances to enter the vial. In addition to assuring sterility, vacuum retention is essential for products stoppered at ambient or reduced pressures to assure safe and proper reconstitution. The material of the stopper forming the gas-seal of the container is preferably an elastomeric compound or multicomponent formulation based on an elastomer, such as poly(isobutylene) or butyl rubber. Conveniently a butyl rubber stopper from Daiko Seiko ltd. can be used.

EXAMPLES

The following materials are employed in the examples:
PBS Phosphate buffered saline: 10 mM sodium phosphate, NaCl 0.9% w/w, pH=7.4
Tris buffer Tris buffered saline: 10 mM Tris (hydroxy methyl)aminomethane, NaCl 0.9%, pH=7.4
HEPES buffer 4-(2-hydroxyethyl)-1-piperazineethanesulfonic acid (20 mM) and NaCl (150 mM), pH=7.4
Tris glycerol buffer Tris(hydroxymethyl)aminomethan 1 g/l and 0.3 M glycerol, pH=7.2
DIO18 marker 3,3'-dioctadecyloxacarbocyanine (Molecular Probes Inc., U.S.A.)
Gd-DTPA-(SE)$_2$ Distearoyl ester of gadolinium-diethylenetriaminepentacetic acid complex (prepared according to G. W. Kabalka et al., Magnetic Resonance in Medicine 8 (1988), 89-95)
DSPG Distearoylphosphatidylglycerol sodium salt (Genzyme) IUPAC: 1,2-Distearoyl-sn-glycero-3-[phospho-rac-(1-glycerol)]
DAPC Diarachidoylphosphatidylcholine (Avanti polar Lipids) IUPAC: 1,2-Diarachidoyl-sn-glycero-3-phosphocholine
DSTAP 1,2-Distearoyl-3-trimethylammonium-propane chloride (Avanti Polar Lipids)
DSPC Distearoyl phosphatidylcholine (Genzyme) IUPAC: 1,2-Distearoyl-sn-glycero-3-phosphocholine
DPPG Dipalmitoylphosphatidylglycerol sodium salt (Genzyme) IUPAC: 1,2-Dipalmitoyl-sn-glycero-3-[phospho-rac-(1-glycerol)]
DPPA Dipalmitoyl phosphatidic acid sodium salt (Genzyme) IUPAC: 1,2-Dipalmitoyl-sn-glycero-3-phosphate
DPPC Dipalmitoyl phosphatidylcholine (Genzyme) IUPAC: 1,2-Dipalmitoyl-sn-glycero-3-phosphocholine DSEPC Distearoylethylphosphatidylcholine (Avanti Polar Lipids) IUPAC: 1,2-Distearoyl-sn-glycero-3-Ethylphosphocholine NaDOC sodium deoxycholate (Fluka)

DSPE-PEG2000 Distearoylphosphatidylethanolamine modified with PEG2000, sodium salt (Nektar Therapeutics)

Ethyl-SPC3 Soy ethyl phosphocholine: 4:1 (w/w) mixture of Ethyl-DSPC and Ethyl-DPPC DPPE-cap-biotin 1,2 dipalmitoyl-sn-glycero-3-phosphoethanolamine-N-(cap biotinyl) sodium salt (Avanti Polar Lipids)

PEG4000 Polyethyleneglycol, MW=4000 (Fluka)

Pluronic 68 Ethyleneoxide/propyleneoxide block copolymer (Fluka)

$C_4F_{10}$ Perfluorobutane

Dimensions and concentration of microvesicles are determined by using Coulter counter Multisizer (aperture: 30 μm).

ζ-potentials of microvesicles suspensions are determined by using a Malvern Zetasizer 3000Hsa in NaCl 1 mM.

Dimensions of micelle preparations are determined using a Malvern Zetasizer 3000Hsa.

Example 1

Preparation of Positively Charged Microballoons

Tripalmitin (60 mg) is dissolved in cyclohexane (0.6 ml) at 40° C. This organic phase is kept at 40° C. until emulsification. 40 mg of Ethyl-SPC3 (cationic phospholipid) are dispersed in 30 ml of distilled water at 65° C. for 15 min and then the dispersion is allowed to cool to 40° C.

The organic phase is emulsified in the aqueous phase using a Polytron® homogeniser PT3000 (10000 rpm, 1 min). The emulsion is then diluted with 5 ml of PVA (200 mg, Mw: 9000 from Aldrich) in distilled water, then cooled to 5° C., frozen at −45° C. for 10 min and then lyophilized (0.2 mbar, 24 h).

The lyophilisate is redispersed in distilled water (20 ml) in the presence of air, microballoons are washed twice by centrifugation (600 g for 10 min) with phosphate buffered saline and the final suspension of microballoons (20 ml). The size characterization for this preparation gave the following results: $D_{V50}$=2.54 μm; $D_N$=1.57 μm.

Example 1a

Preparation of Fluorescent Marked Positively Charged Microballoons

Example 1 is repeated by adding 5% by weight (with respect to the total weight of tripalmitin) of lipophilic fluorescent probe DIO18 in the organic phase for fluorescently marking the microballoon. The size characterization for this preparation gave the following results: $D_{V50}$=2.38 μm; $D_N$=1.45 μm.

Examples 2a-2e

Preparation of DSTAP-containing Positively Charged Microbubbles 15 mg of a mixture of DAPC and cationic lipid DSTAP (see relative ratio in table 1) and 985 mg PEG4000 are dissolved in tert-butanol (10 ml) at 50° C. The solution is sampled in 10 ml vials (50 mg of dry matter per vial) then freeze dried in a Christ Epsilon 2-12DS freeze dryer (−30° C., 0.56 mbar for 24 h). After additional drying (25° C., 0.1 mbar for 5 hours), the vials are stoppered with an elastomeric stopper and sealed with an aluminium flip off.

The obtained lyophilisates are exposed to the desired gas (50:50 v/v of $C_4F_{10}/N_2$) and then redispersed in 5 ml of the PBS buffer solution thus obtaining a suspension of positively charged microbubbles. Size characterization of suspended microbubbles is reported in table 1.

TABLE 1

| DSTAP-containing microbubbles | | | |
|---|---|---|---|
| Example | DAPC/DSTAP molar ratio | $D_V$ | $D_N$ |
| 2a | 99:1 | 8.57 | 3.11 |
| 2b | 95:5 | 8.64 | 1.73 |
| 2c | 90:10 | 8.80 | 1.77 |
| 2d | 80:20 | 9.22 | 1.82 |
| 2e | 50:50 | 8.51 | 1.94 |

Examples 3a-3c

Preparation of Negatively Charged Microbubbles

The preparation of examples 2a-2e is repeated by replacing the DAPC/DSTAP mixture with the same total amount (15 mg) of a DPPG/DSPC mixture in different relative amounts, as indicated in Table 2. Size characterization of suspended microbubbles is reported in table 2.

TABLE 2

| DPPG-containing microbubbles | | | |
|---|---|---|---|
| Example | DSPC/DPPG molar ratio | $D_V$ | $D_N$ |
| 3a | 75:25 | 6.05 | 1.97 |
| 3b | 50:50 | 12.97 | 1.97 |
| 3c | 25:75 | 5.89 | 1.88 |

Example 4

Preparation of Positively Charged Microbubbles

DSTAP (200 mg) is dispersed in 100 ml of water containing 5.4% (w/w) of a mixture of propylen glycol and glycerol (3:10 w/w) at 80° C. for 5 minutes and then cooled to room temperature.

The dispersion is transferred in a reactor under $C_4F_{10}$ atmosphere and homogeneised at 20000 rpm (Polytron PT3000) for 10 min, keeping the rotor stator mixing shaft such that the openings are slightly above the surface of the liquid. The obtained microbubbles are washed twice by centrifugation with water, then redispersed in a dextran 7.5% solution.

The suspension is sampled in 10 ml vial (2 ml per vial). The vials are cooled to −45° C. and lyophilized for 24 hours, then stoppered, sealed and kept at room temperature. Size characterization of microbubbles re-suspended in distilled water was as follows: $D_V$=4.04; $D_N$=1.75.

Example 5a-5d

Preparation of Negatively Charged Micelles 50 mg of Gd-DTPA-(SE)$_2$ (containing traces of radioactive $^{153}$Gd) and 10 mg of NaDOC are dispersed in 5% aqueous glucose (10 ml) using a 3 mm sonication probe attached to a Branson 250 sonifier (output: 30% for 10 min), to obtain an aqueous suspension of anionic micelles. The same preparation is repeated by dispersing different amounts of different compounds in the same volume of aqueous glucose solution, as indicated in the following table 3.

TABLE 3

Negatively charged micelles

| Example | Gd-DTPA-(SE)$_2$ (mg) | NaDOC (mg) | DPPE-Cap-Biotin (mg) | DPPA (mg) | Pluronic F68 (mg) |
|---|---|---|---|---|---|
| 5a | 50 | 10 | — | — | — |
| 5b | 50 | 10 | 3.8 | — | — |
| 5c | — | — | — | 16 | 16 |
| 5d | — | — | 2.5 | 16 | 16 |

Example 6a-6f

Preparation of DPPA-containing Negatively Charged Micelles

Various amounts of anionic phospholipid DPPA and neutral phospholipid DPPC (as indicated in table 4) together with 16 mg Pluronic F68 are dispersed in 10 ml of PBS, using a 3 mm sonication probe (Branson 250 sonifier, output 30% for 10 min). A small amount of DPPC-H$^3$ (approximately 2.5 µCi for 10 ml of final suspension) is added to the micelle preparation as radioactive marker.

After sonication, the solution is filtered through 0.2 µm filters (Millipore). After cooling to room temperature, micelle size is measured using Malvern Zetasizer 3000HSA and specific radioactivity is determined using 50 µl of solution diluted in 10 ml of LSC cocktail Hionic Fluor (Packard Bioscience) and counted in Tricarb 2200A liquid scintillation analyzer (Packard Bioscience).

TABLE 4

DPPA containing negative micelles

| Example | DPPC (mg) | DPPA (mg) | DPPA/DPPC molar ratio | Pluronic F68 (mg) | Amount of DPPA (% w/w) |
|---|---|---|---|---|---|
| 6a | 17.62 | 0 | — | 16.0 | — |
| 6b | 17.30 | 0.16 | 1:99 | 16.0 | 0.48 |
| 6c | 17.26 | 0.32 | 2:98 | 16.0 | 0.95 |
| 6d | 15.86 | 1.61 | 10:90 | 16.0 | 4.81 |
| 6e | 8.80 | 8.00 | 50:50 | 16.0 | 24.39 |
| 6f | 0.88 | 15.27 | 95:5 | 16.0 | 47.5 |

Example 7a-7b

Preparation of Negatively Charged Micelles Containing DSPE-PEG 20 mg of DSPE-PEG 2000 are dissolved in 1 ml of chloroform/ethanol (1/1, v/v) at 60° C. in a round bottom flask and the solvent mixture is evaporated under vacuum, leaving a thin film on the inner wall of the flask. This film is further dried overnight in a vacuum chamber. The lipid film is then hydrated with 10 ml Hepes buffer at 60° C. for 30 min. The solution is then filtered on 0.2 µm filters and allowed to cool to room temperature prior to characterization. The filtered solution is diluted in water (dilution ratio 1:3) and analyzed by Malvern Zetasizer 3000HSA for size distribution. The results of two different preparations according to the above procedure are summarized in Table 5.

TABLE 5

| Example | Dv (nm) | Dn (nm) |
|---|---|---|
| 7a | 15 | 9.9 |
| 7b | 10.4 | 4.4 |

Example 8

Preparation of Positively Charged Micelles Containing Ethyl-SPC3

16 mg of Ethyl-SPC3 and 16 mg of Pluronic F68 are dispersed in 5% aqueous glucose (10 ml) using a 3 mm sonication probe attached to a Branson 250 sonifier (output: 30% for 10 min), to obtain an aqueous suspension of cationic micelles.

Examples 9a-9e

Preparation of DSTAP-containing Positively Charged Micelles

The preparation of examples 6a-6f is repeated by replacing negatively charged DPPA with positively charged DSTAP. Relative amounts of lipids and phospholipids of the different preparations are reported in table 6.

TABLE 6

DSTAP-containing positively charged micelles

| Example | DPPC (mg) | DSTAP (mg) | DPPC/DSTAP Molar ratio | Pluronic F68 (mg) |
|---|---|---|---|---|
| 9a | 17.62 | 0 | — | 16.0 |
| 9b | 17.44 | 0.17 | 99:1 | 16.0 |
| 9c | 17.26 | 0.34 | 98:2 | 16.0 |
| 9d | 15.86 | 1.69 | 90:10 | 16.0 |
| 9e | 8.81 | 8.43 | 50:50 | 16.0 |

Examples 10a-10b

Preparation of Assemblies with Cationic Microballoons and Anionic Micelles

The microballoons suspension of example 1 (1 ml) is admixed with different volume amounts (indicated in table 7) of the micelle preparation of Example 5a or of Example 5b, respectively. After 1 hour, the suspension is washed twice with PBS by centrifugation (600 g for 5 min) and redispersed in PBS (1.2 ml). The amount of bound micelles (expressed as the percentage of the radioactivity measured on the assembly suspension with respect to the radioactivity measured on the initial micelle preparation) is determined by measuring the Gd$^{153}$ radioactivity (gamma count) of the suspension, by using a Cobra II Autogamma instrument (Packard Bioscience). The results are given in table 7.

TABLE 7

| | µl micelle/ml microballoons | DV50 (µm) | DN (µm) | % of bound micelles |
|---|---|---|---|---|
| Example 1 | — | 2.38 | 1.45 | — |
| Example 10a (assembly with non-biotinated micelles of ex. 5a) | 2.5 | 2.69 | 1.66 | 100 |
| | 10 | 2.83 | 1.70 | 90.9 |
| | 25 | 2.81 | 1.71 | 91.4 |
| | 100 | 2.37 | 1.58 | 31.1 |

TABLE 7-continued

|  | μl micelle/ml microballoons | DV50 (μm) | DN (μm) | % of bound micelles |
|---|---|---|---|---|
| Example 10b (assembly with biotinated micelles from ex. 5b) | 2.5 | 2.63 | 1.66 | 100 |
|  | 10 | 2.84 | 1.70 | 96.8 |
|  | 25 | 2.84 | 1.73 | 88.1 |
|  | 100 | 2.43 | 1.62 | 30.1 |

As inferable from the above table, while the relative amount of bound micelles (i.e. the percentage of bound micelles with respect to the total amount of added micelles) decreases by increasing the total amount of micelles (i.e. the volume of micelle suspension) added to the microvesicle suspension, the absolute amount of bound micelles (given by the product of the first and last column in table 7) is nevertheless increasing.

Substantially similar results are obtained by preparing an assembly with the microballoons of example 1 and the micelle preparations of examples 5c or 5d, respectively.

Example 11

Determination of Binding Activity of the Assemblies of Example 10a-10b

To test the binding activity of the assemblies of examples 10a and 10b (10 μl and 100 μl of each micelle suspension preparations), a neutravidin coated surface is prepared as follows:

Carbonate Buffer (pH 9.5-300 μl) and NeutrAvidin™ (Pierce −1 mg/ml-50 μl) are added to each well of a twelve wells plate (Nunc™). After incubation (overnight −4° C.), the well is washed twice with PBS containing Tween 20 0.1% and twice with PBS. Bovine serum albumin (2% in PBS-350 μl) is added and after incubation (25° C.-1 h), the well is washed twice with PBS containing Tween 20 0.1% and twice with PBS.

An amount of $2 \cdot 10^8$ assemblies prepared according to examples 10a and 10b are added to each well, then the well is filled with PBS, sealed and the plate is turned. After inverse incubation (2 h-25° C.), the well is washed twice with PBS and the surface is observed through an optical microscope with a 40× magnification lens. Both the assemblies from example 10b, containing biotinated micelles, show affinity for the neutravidin coated surface, the 100 μl/ml preparation providing a higher coverage of the surface with respect to the 10 μl/ml preparation. Corresponding non-biotinated preparations of example 10a show instead no binding activity on the neutravidin coated surface.

Substantially similar results are obtained by comparing the binding activity of assemblies comprising microballoons of example 1 and non-biotinated micelles of example 5c with corresponding assemblies comprising microballoons of example 1 and biotinated micelles of example 5d.

Example 12a-12b

Preparation of Assemblies with Cationic Microbubbles and Anionic Micelles

The microbubbles suspension of example 2d (1 ml) is admixed with different volume amounts (indicated in the following table 8) of the micelle preparation of Examples 5a or 5b, respectively. Suspensions are gently stirred for 1 hour then washed twice by centrifugation (180 g for 5 min) with Tris glycerol buffer. Infranatant is discarded and the residue is dispersed in Tris glycerol buffer (1 ml). Size, concentration and ζ-potential of the obtained assemblies are reported in table 8.

TABLE 8

|  | micelle/microbubble susp. (μl/ml) | DV50 (μm) | DN (μm) | ζ-potential (mV) |
|---|---|---|---|---|
| Example 2d | — | 4.74 | 1.82 | 57.1 |
| Example 12a | 10 | 6.92 | 2.75 | 37.6 |
| (with non-biotinated | 30 | 8.79 | 2.81 | −19.0 |
| micelles from example | 100 | 7.81 | 2.29 | −38.0 |
| 5a) | 300 | 6.12 | 1.91 | −50.4 |
| Example 12b | 10 | 6.43 | 2.53 | 30.1 |
| (with biotinated | 30 | 7.31 | 2.37 | −28.2 |
| micelles from example | 100 | 7.22 | 1.94 | −42.4 |
| 5b) | 300 | 6.11 | 1.87 | −44.4 |

In both cases, increasing volumes of micelle suspension determine a reduction of the ζ-potential of the obtained respective assembly suspension.

Substantially similar results are obtained by using the microbubbles suspensions of examples 2c or 2e, in place of the microbubble suspension of example 2d, or by replacing the micelle preparations of examples 5a and 5b with those of examples 5c and 5d, respectively.

Example 13

Determination of Binding Activity of the Assemblies of Examples 12a-12b

To test the binding activity of the assembly of example 12a-12b, a neutravidin coated surface is prepared as described in example 11 and tested with different amounts (300, 100, 30 and 10 μl) of the preparations of examples 12a and 12b.

A marked binding activity is observed at the optical microscope for the 100 μl/ml and 300 μl/ml preparations of example 12b. A lower binding is observed for the 30 μl/ml preparation while the 10 μl/ml mixture shows poor binding. All the assemblies of example 12a (not containing biotinated micelles) show no binding activity.

Example 14a-14b

Preparation of Assemblies with Cationic Microbubbles and Anionic Micelles

The lyophilized content of a vial obtained according to example 4 is exposed to $C_4F_{10}$ and redispersed in 2 ml of distilled water. The suspension is washed twice by centrifugation (180 g for 10 min) with PBS and redispersed in 2 ml of PBS.

50 μl of a micelles preparation prepared according to example 5a or 5b, respectively, are added, the mixture is stirred overnight with a rotating stirrer under $C_4F_{10}$ atmosphere, then washed twice with PBS by centrifugation (180 g for 10 min) and finally redispersed in 2 ml of PBS.

Table 9 provides the characterization of the assemblies of examples 14a and 14b.

TABLE 9

|  |  | $DV_{50}$ (μm) | $D_N$ (μm) | Conc. (part./ml) | Micelles Yield (%) |
|---|---|---|---|---|---|
| Example 14a | Microbubbles | 4.57 | 2.75 | 5.50E+08 | — |
|  | Assemblies | 4.81 | 2.72 | 4.04E+08 | 91.9 |

TABLE 9-continued

|  | DV$_{50}$ (μm) | D$_N$ (μm) | Conc. (part./ml) | Micelles Yield (%) |
|---|---|---|---|---|
| Example 14b Microbubbles | 4.39 | 2.65 | 3.48E+08 | — |
| Assemblies | 4.45 | 2.44 | 3.45E+08 | 83.8 |

As inferable from the above table, the substantial totality of the micelles is associated to microbubbles in the formed assemblies, said assemblies having substantially the same mean diameter as the initial microbubbles.

Example 15

Preparation of Assemblies with Anionic Microbubbles and Cationic Micelles

A microbubbles suspension prepared according to example 3b (1 ml) is admixed with different volume amounts (indicated in the following table 10) of the micelles preparation of Example 8. The suspension is gently stirred for 1 hour, then washed twice by centrifugation (180 g for 5 min) with Tris glycerol buffer. Infranatant is discarded and the resulting assemblies are dispersed in Tris glycerol Buffer (1 ml). Table 10 shows some characteristics of the assemblies.

TABLE 10

| μl micelles suspension per ml of microbubbles suspension | D$_V$ (μm) | D$_N$ (μm) | ζ-potential (mV) |
|---|---|---|---|
| 0 | 7.87 | 1.86 | −60.2 |
| 10 | 11.43 | 4.98 | −44.9 |
| 100 | 9.16 | 2.48 | +17.1 |
| 300 | 9.20 | 2.12 | +49.4 |

It can be observed that with an amount of micelles capable of determining a reversal in sign of the initial ζ-potential of the microbubbles suspension, the mean dimensions of the assembly become closer to the dimensions of the initial microbubbles.

Example 16

Determination of the Amount of Bound Micelles as a Function of the Amount of Charged Compounds in Assembly Preparations Comprising Cationic Microbubbles and Anionic Micelles Different assembly suspensions are prepared by admixing 300 μl of a micelle solution prepared according to examples 6a-6f to 1 ml of a microbubble suspension in PBS prepared according to examples 2a-2e in a 5 ml glass tube, for a total of 30 assembly preparations. The mixed suspensions are gently stirred for 30 min and then washed twice by centrifugation (180 g for 10 nm) to remove unbound material. The amount of the lipid molecules in micelles bound to the microbubbles is evaluated by dosing radioactively labelled molecule DPPC-$^3$H incorporated within the micelles.

FIG. 1 shows the results of the measurements, where lines A to E represent the amounts of micelles bound to the microvesicles as a function of the amount of charged compounds in said micelles, for assemblies comprising the respective microvesicles prepared according to examples 2a to 2e.

From said figure, it can be noticed that substantially no bound micelles are observed for assembly preparations including micelles of example 6a (no charged surfactant). Furthermore, the amount of micelles bound to the microvesicles increases with the increase of the amount of charged compounds included in the microvesicle. Finally, for this particular combination of micelles/microvesicles assemblies, it can be observed that higher amounts of micelles bind to the microvesicles when the relative amount of charged compound in the micelle is from about 1% to 5% (w/w) of the total weight.

Example 17

Determination of the Amount of Bound Micelles as a Function of the Amount Of Charged Compounds in Assembly Preparations Comprising Anionic Microbubbles and Cationic Micelles Different assembly suspensions are prepared by admixing 300 μl of each of the micelle solutions prepared according to examples 9a-9e to 1 ml of each of the microbubble suspensions prepared according to examples 3a-3c in a 5 ml glass, respectively, for a total of 15 assembly preparations. The mixed suspensions are gently stirred for 30 min and then washed twice by centrifugation (180 g for 10 nm) to remove unbound material. The amount of the lipid molecules in micelles bound to the microbubbles is evaluated by dosing radioactively labeled molecule DPPC-$^3$H incorporated within the micelles.

Similar results are observed as for the assembly preparations of example 16, i.e. that by increasing the amount of charged compounds included in the microvesicle it is possible to increase the amount of micelles bound to the microvesicles and that, in particular for assemblies where the microvesicles contain a lower amount of charged compounds, a higher amount of micelles is bound to the microvesicles when the relative amount of charged component in the micelle is from about 1% to 5% (w/w).

Example 18

Determination of the Amount of Bound Micelles as a Function of the Amount Of Micelles Added to Microbubbles Suspensions Including Different Amounts of Charged Compounds Different amounts (50, 100, 250 and 500 μl) of micelle preparations prepared according to example 7a or 7b are combined with 1 ml of the microbubble preparations prepared according to examples 2b, 2d and 2e for a total of 12 assembly preparations (in particular 2b and 2d are combined with 7a, while 2d is combined with 7b). The mixtures are gently stirred for 30 min, and washed twice by centrifugation (180 g/10 min) in water to remove the unbound material.

The resulting suspensions are characterized by Coulter Counter for the measurement of size distribution and by Malvern Zetasizer for ζ-potential. A portion of the samples is freeze-dried at 0.2 mbar for 24 hours and the lyophilisate analyzed by HPLC to determine the amount of DSPE-PEG in the assemblies (μg PE-PEG/ml bubbles). The results are summarized in the following table 11, illustrating the initial amount of DSPE-PEG included in the mixture for forming the assembly, the final amount of DSPE-PEG in the assembly (corresponding to the amount of bound micelles), the ratio (expressed as equivalent of charges) between positive and negative charges in the final assembly and the respective ζ-potential of the final suspension.

TABLE 11

Cationic microbubbles and anionic micelles

| | Initial mixture | Final mixture | | |
|---|---|---|---|---|
| | DSPE-PEG (nmoles) | DSPE-PEG (nmoles) | EC ratio | ζ-potential (mV) |
| Examples 2d and 7a | 35.87 | 1.35 | 0.18 | 35.8 |
| | 71.75 | 2.34 | 0.43 | 15.6 |
| | 179.37 | 2.28 | 0.46 | 10.9 |
| | 358.75 | 3.26 | 0.59 | −13.3 |
| Examples 2d and 7a | 35.87 | 3.30 | 0.14 | 26.2 |
| | 71.75 | 3.69 | 0.18 | 20.8 |
| | 179.37 | 3.36 | 0.21 | 12.4 |
| | 358.75 | 4.77 | 0.22 | −10.0 |
| Examples 2e and 7b | 35.87 | 3.81 | 0.07 | 39.3 |
| | 71.75 | 5.24 | 0.10 | 31.5 |
| | 179.37 | 8.04 | 0.15 | 18.3 |
| | 358.75 | 9.79 | 0.20 | 9.6 |

From the above table, it can be observed that, in general, the higher the amount of charged compounds in the microvesicle, the higher the amount of bound micelles in the final assembly. In addition, with respect to a same microbubble preparation, the higher the amount of bound DSPE-PEG, the higher the EC ratio and the lower the respective ζ-potential value.

Example 19

Assembly of Cationic Microvesicles with Anionic Micelles and Comparative Mixture of Anionic Microvesicles and Anionic Micelles 20 mg of DSPE-PEG 2000 are weighted and dissolved in chloroform/Methanol (1/1, v/v) at 60° C. in a round bottom flask and the solvent mixture is evaporated under vacuum, deposing a thin film on the inner wall of flask. This film is further dried overnight in a vacuum chamber.

The lipid film is hydrated with 10 ml 5% glucose at 60° C. during 30 min, the solution is filtered on 0.2 μm filters and then cooled down to room temperature prior to the characterization.

The preparation is repeated twice.

Microbubbles are prepared as described in example 2e (positively charged) and 3b (negatively charged), by using a 50/50 (w/w) mixture of DAPC and DSTAP or a 50/50 (w/w) mixture of DSPC and DPPG. Vials are exposed to $C_4F_{10}/N_2$ 50/50 (v/v) prior to reconstitution.

2.5 ml of micelles solution are diluted with 2.5 ml of 5% glucose. The lyophilized microbubbles are reconstituted using the diluted solution of micelles, vortexed for 2 minutes then mixed gently for 30 minutes.

The obtained suspension is washed twice with glucose 5% (by centrifugation, 180 g/10 min) and the supernatant is redispersed in 2.5 ml of 5% glucose. ζ-potential of each suspension is measured by using a Malvern Zetasizer 3000Hsa (50 μl/10 ml NaCl 1 mM). The amount DSPE-PEG2000 in each suspension is determined using HPLC. Results are given in the following table 12.

TABLE 12

Mixture of anionic micelles with anionic or cationic microbubbles

| Anionic micelle suspension with: | ζ-potential (mV) | DSPE-PEG2000 (μg/ml) |
|---|---|---|
| Anionic microbubbles | −41.3 ± 2.7 | 0.8 |
| Cationic microbubbles | −18.3 ± 2.5 | 129.0 |

From the above table, it can be observed that substantially no binding of anionic micelles on anionic microbubbles is obtained, i.e. only negligible amounts of DSPE-PEG are found in the final mixture, while the ζ-potential remains substantially negative.

Example 20

Cationic Microballoons—Colloidal Gold Assembly

A suspension of cationic microballoons prepared according to example 1 is admixed with a colloidal suspension of gold particles stabilized with sodium citrate (Polysciences—60 nm) in various ratios (expressed as number of gold particles/number of microballoons, see table 13). After 2 hours, the floating particles are separated and redispersed in distilled water. Table 13 shows that a neutral value of ζ-potential is achieved at a ratio of about 200 gold particles per microballoon.

TABLE 13

| Gold colloid/Microballoons Number ratio | Cationic microballoons |
|---|---|
| 0 | +35.0 |
| 50 | +23.8 |
| 100 | +19.3 |
| 200 | −0.7 |
| 800 | −2.8 |
| 2000 | −19.0 |

Example 21

Cationic Microbubbles-magnetites Assembly

Magnetites coated with DPPA/Pluronic F108 (FE/DPPA/Pluronic F108 ratio 3/15/15 in mg/ml) were prepared according to U.S. Pat. No. 5,545,395. The solution was diluted 100 times with Tris(1 g/l)/Glycerol(0.3M) buffer (pH:7.05). Cationic microbubbles (prepared according to example 2d, except that the Employed gas is $SF_6$ instead of the $C_4F_{10}/N_2$ mixture) are redispersed under $SF_6$ atmosphere with 5 ml of magnetites solution. After 2 min of vortexing, the suspension is mixed gently for 1 hour. Then the floating particles are washed twice with Tris/Glycerol buffer by centrifugation (180 g/10 min). Size and concentration are measured by Coulter counter Multisizer. ζ-potential is determined with Malvern Zetasizer 3000Hsa (dilution: 50 μl/10 ml water). Magnetites binging was measured using relaxation time (T2) determination (Bruecker: Minispec MQ20) and compared with a control carried out on a same prepared of microbubbles without magnetite particles. The results are given in table 14.

TABLE 14

| | Control suspension (without magnetite particles) | Suspension with magnetite particles |
|---|---|---|
| ζ-potential (mV) | +40.4 ± 0.8 | −30.8 ± 4.1 |
| T2 (ms) | 1800 ± 300 | 29.3 ± 0.2 |

As shown in the above table, further to the reduction of the ζ-potential with respect to the control suspension a substantial reduction of the T2 is observed, confirming a substantial binding of magnetite-containing micelles to the microbubbles.

Example 22

Effect of Opposite Charged Micelles on the Surface of Charged Microbubbles in In Vivo Administration Positively charged microbubbles are prepared as described in example 2d using a 80/20 (w/w) mixture of DAPC and DSTAP. Negatively charged microbubbles are prepared as described in example 3b using a 50/50 (w/w) mixture of DSPC and DPPG. Vials are exposed to $C_4F_{10}/N_2$ 50/50 (v/v) prior to reconstitution with Tris/glycerol buffer (5 ml).

Micelles are prepared according to example 6f (negatively charged) and example 8 (positively charged). Thereafter the following suspensions of microbubbles or of assemblies are prepared:

Suspension A: 600 μl of Tris/Glycerol buffer are admixed with 2 ml of microbubbles (example 2d—positively charged) and mixed gently for 30 min.

Suspension B: 600 μl of micelles according example 6 g (negatively charged) are admixed with 2 ml of microbubbles (example 2d—positively charged) and mixed gently for 30 min.

Suspension C: 600 μl of Tris/Glycerol buffer are admixed with 2 ml of microbubbles (example 3b—negatively charged) and mixed gently for 30 min.

Suspension D: 600 μl of micelles according example 8 (positively charged) are admixed with 2 ml of microbubbles (example 3b—negatively charged) and mixed gently for 30 min.

All suspensions are washed twice with Tris/glycerol buffer (by centrifugation 180 g/10 min) and the supernatants are redispersed in 2 ml of buffer. Sizes and concentrations are determined using a Coulter counter. ζ-potential of each suspension is measured with a Malvern Zetasizer 3000Hsa (50 μl/10 ml NaCl 1 mM) and are illustrated in the following table 15.

TABLE 15

| Suspension | ζ-potential (mV) |
|---|---|
| A | +48.6 ± 9.3 |
| B | −51.9 ± 1.3 |
| C | −61.5 ± 7.2 |
| D | +37.2 ± 9.8 |

Figure 2:
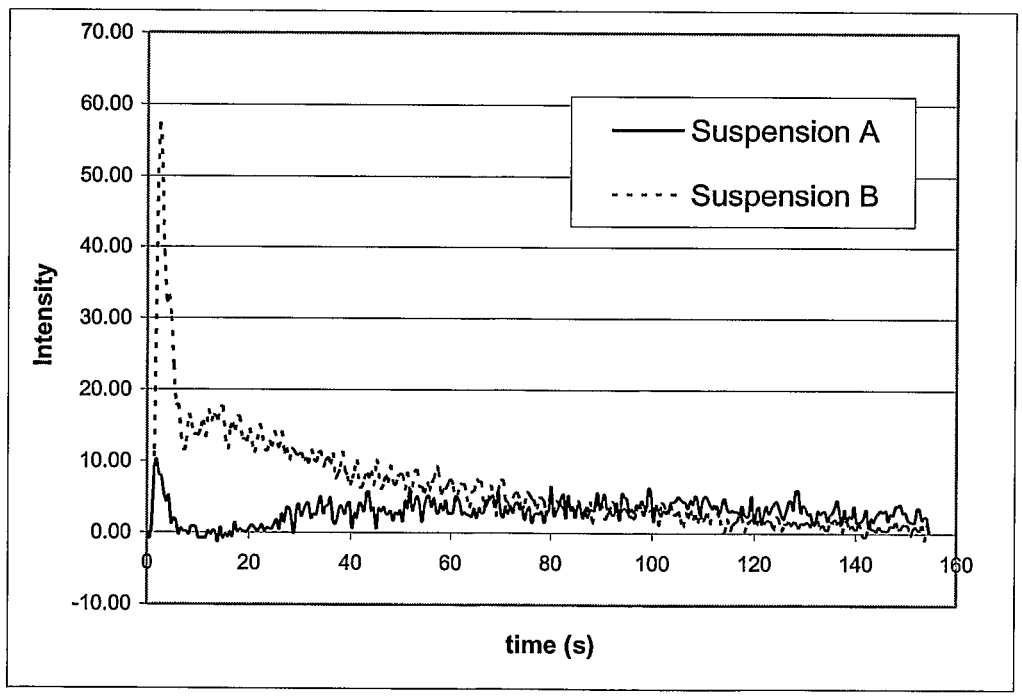
FIGS. 2 and 3 show the in vivo behaviour of charged microvesicles and of corresponding assemblies with MACs of opposite charge with respect to the microvesicle.
Figure 3:
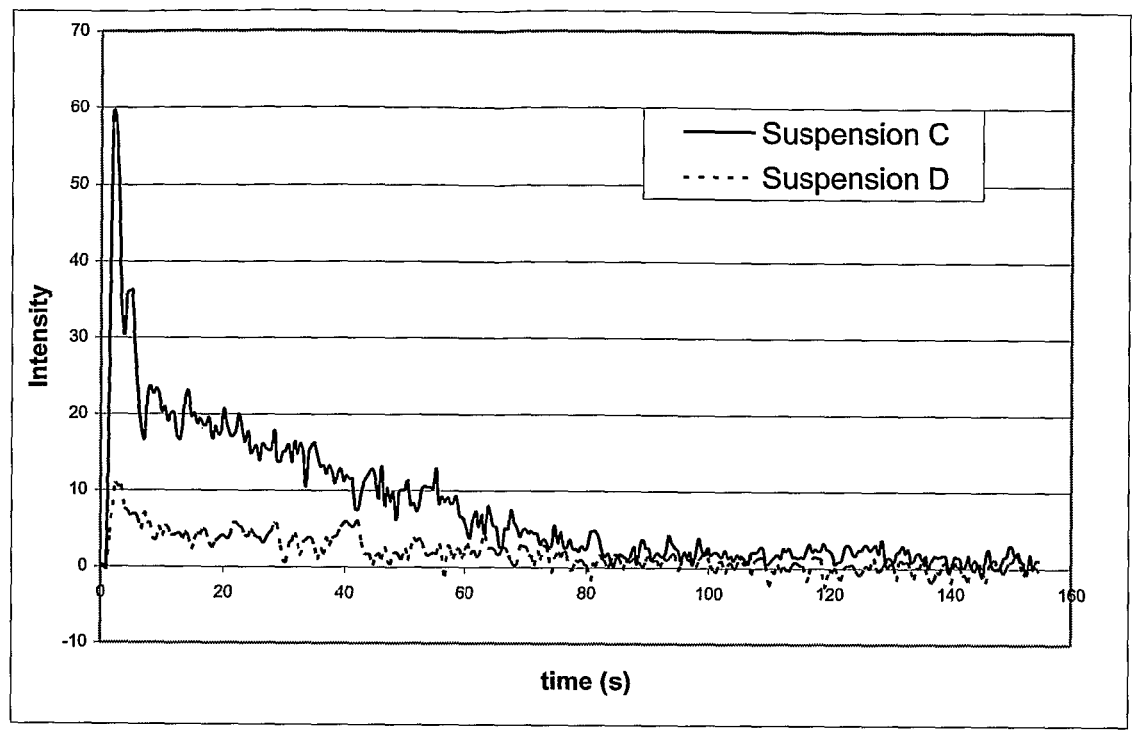

The suspensions were injected in a rabbit ear vein at a dose of 5E+06 microbubbles per kg body weight. Two-dimensional echography was performed in Coherent Contrast Imaging (CCI) using an Acuson Sequoia 512 equipped with a 4C1-S transducer in intermittent imaging (two frames/s) and a high mechanical index (MI). Images of the kidney were recorded on a video recorder during 3 minutes and the sequence was analyzed to determine the mean pixel intensity as a function of time in a region of interest (ROI) selected in the cortex (FIGS. 2 and 3).

As seen on the figures, the addition of micelles of opposite charge on microbubbles changes dramatically the in vivo behaviour of microbubbles. Thus positively charged bubbles are hardly detectable in the cortex of the kidney (suspension A). However after incubation with negatively charged micelles, the same microbubbles show a strong signal in the ROI (suspension B). Similarly negatively charge microbubbles (suspension C) show a strong signal in the kidney. However after admixture with positively charged micelles, almost no signal is detectable in the ROI.

Example 23

Assembly of Cationic Microbubbles with Anionic Micelles Comprising a Drug 2 ml of microbubble suspension (prepared according to example 2a dispersed in PBS) are mixed with different amounts of Fungizone® solutions (micellar suspension of Amphotericin B with sodium deoxycholate in PBS—Bristol Myers Squibb) as illustrated in the following table 16. Suspensions are gently stirred for 1 hour, then washed twice by centrifugation (180 g/5 min) with PBS buffer. Infranatant is discarded and the obtained assemblies are dispersed in Buffer (1 ml). Size and concentration are measured by Coulter Counter Multisizer (aperture: 30 μm-50 μl/100 ml NaCl 0.9%). ζ-potential is determined with a Malvern Zetasizer 3000Hsa (50 μl/10 ml distilled water). The amount Amphotericin B on microbubbles was measured by spectrophotometry (409 nm -50 μl of assemblies in 2 ml of $CHCl_3$/MeOH 1/1) and compared to a calibration curve of Fungizone®. The results illustrated in the following table 16 show that by increasing the amount of added micelles, it is possible to include increasing amounts of drug in the assemblies.

TABLE 16

Assemblies with drug

| | μl of micelles suspension per ml of microbubbles suspension | ζ-potential (mV) | Amphotericin B (μg/ml) |
|---|---|---|---|
| Ex. 2a | — | 49.1 ± 3.0 | — |
| +Fungizone ® | 10 | 50.8 ± 4.3 | 42.8 |
| | 30 | 28.9 ± 6.9 | 122.0 |
| | 100 | −24.7 ± 0.3 | 367.9 |

Example 24

Assembly with Double Layer of Micelles

Ex. 24a: Preparation of Negatively Charged Bubbles

DPPC/DPPS-containing microbubbles are prepared using the method similar to the one described in Example 3 of U.S. Pat. No. 5,830,435. Briefly, multilamellar liposomes (MLVs) are obtained by dispersing 59.2 mg of DPPC and 40.8 mg of DPPS in 100 ml of distilled water containing 1 g of propylene glycol. The liposomes are incubated at 70° C. for 30 min under agitation. The mean diameter of the liposomes is of about 1.4 μm for $D_N$ and 2.7 μm for $D_V$.

The liposome suspension is introduced in a gas tight glass reactor equipped a high speed mechanical emulsifier (Megatron MT3000, Kinematica, Switzerland). A gas bag containing $C_4F_{10}$ is connected to the mixing chamber of the emulsifier. After homogenisation (10,000 rpm, 1 min), a milky suspension of microbubbles is obtained. The infranatant (about 90 ml containing mostly liposomes) is removed by decantation. The supernatant (containing the microbubbles) is recovered and resuspended in distilled water to a total volume of 100 ml. The decantation step is repeated and the final bubble suspension is resuspended in 10% maltose. Aliquots of the suspension are collected in 10 ml glass vials (1 ml of suspension per vial) and the samples are frozen at −45° C. and lyophilized.

After lyophilisation, the vials are closed with rubber stoppers, evacuated and filled with a gas mixture containing a 1:1 (v/v) mixture of $C_4F_{10}$ and air. Microbubbles are generated by injecting 2 ml distilled water into the vials through the stopper and hand shaking.

Ex. 24b: Preparation of Cationic and Anionic Micelles

Ex. 24b1

Cationic micelles are prepared with 3.73 mg/ml of DSPE-PTE020 (a multi-arm PEG-phospholipid, NOF Corporation, Japan) and 1.27 mg of cationic phospholipid DPEPC (Dipalmitoyl Glycero-3-Ethylphosphocholine, Avanti® Polar Lipids, Inc. USA).

Ex. 24b2

Anionic and functionalized micelles are prepared with 4.1 mg/ml of DSPE-PEG2000 and 0.9 mg/ml of a GPIIbIIIa binding lipopeptide (DPPE-PEG2000-Lys-Gln-Ala-Gly-Asp-Val, prepared according to example 3 of U.S. Pat. No. 6,139,819).

Both positively and negatively charged micelles are prepared in 5% glucose solution.

Ex. 24c: Preparation of Assembly with Negatively Charged Bubbles and Multi-MACs Layers Having Opposite Electrically Charges 50 µl and 500 µl of cationic micelles prepared according to Ex. 24b1 are respectively added to two preparations containing about $1 \times 10^9$ negatively charged microbubbles prepared according to Ex. 24a. The mixture is gently stirred for 30 min and then washed twice by centrifugation (10'/1000 rpm), with resuspensions in a solution of glucose 5%. Size and zeta potential of the obtained assembly as determined are reported in table 17 below (rows "Assembly 1"). The results show that after coating the negatively charged microbubbles with a layer of cationic micelles, the measured zeta potential of the assembly suspension becomes positive.

100 µl and 250 µl of anionic micelles suspension (prepared according to Ex. 24b2) are then respectively added to the assembly containing 50 µl of cationic micelles and to the assembly containing 500 µl of cationic micelles. The two mixtures are gently stirred for 30 min and washed twice by centrifugation (10'/1000 rpm) with resuspensions in a solution of glucose 5%. The diameters and zeta potential values of the obtained double layer assembly are given in the table 17 below (rows "Assembly 2"); the presence of the second layer of negative micelles determines corresponding negative values of zeta potential.

TABLE 17

| | µl micelles added to $1 \times 10^9$ microbubbles | $D_V$ (µm) | $D_N$ (µm) | ζ-potential (mV) |
|---|---|---|---|---|
| Microbubbles | 0 | 2.4 | 1.3 | −63 |
| Assembly 1 | 50 | 2.5 | 1.4 | +5 |

TABLE 17-continued

| | µl micelles added to $1 \times 10^9$ microbubbles | $D_V$ (µm) | $D_N$ (µm) | ζ-potential (mV) |
|---|---|---|---|---|
| Assembly 1 | 500 | 2.2 | 1.3 | +8 |
| Assembly 2 | 100 | 2.0 | 1.3 | −30 |
| Assembly 2 | 250 | 2.2 | 1.3 | −38 |

Similar assemblies comprising a plurality of alternately charged layers can also be manufactured with others types of MACs, such as liposomes and nanoparticles. For instance, negatively charged microbubbles can be coated with cationic and drug containing liposomes and then with a second layer of anionic micelles bearing targeting moieties.

Example 25

Preparation of Assemblies from Emulsion 50 ml of distilled water containing DAPC and DSTAP (80:20, 2 mg/ml) are heated at 70° C. for 30 minutes then cooled at room temperature. 4 ml of perfluorohexane is emulsified in this aqueous phase using a high speed homogenizer (Polytron, 10,000 rpm, 1 minute). The resulting emulsion shows a median diameter in volume ($D_{v50}$) of 5.0 µm and a mean diameter in number ($D_N$) of 2.7 µm as determined with a Malvern Mastersizer. The emulsion was washed by centrifugation and re-suspended in water. Different amounts of anionic micelles prepared according to example 24b2 are respectively added to three aliquots of the above cationic emulsion, with respective concentrations of 135 µl, 270 µl and 540 µl per ml of emulsion. After incubation (30 min at room temperature under gentle stirring) and removal of the excess of micelles by centrifugation, the micelle-coated emulsion was redispersed in a 20% (w/w) aqueous PEG4000 solution. The emulsion-micelles assembly was distributed in vials (2 ml/vial) then frozen and lyophilized in vials. Air in the vials of lyophilisates was evacuated and replaced by $C_4F_{10}$. After reconstitution with 2 ml of a 5% glucose solution, a milky microbubble-micelles assembly suspension is obtained. were performed. Results of Coulter counter and zeta potential analyses are gathered in table 18 below.

TABLE 18

| Micelles/bubbles (µl/ml) | Bubbles/ml | $D_N$ (µm) | $D_V$ (µm) | $D_{V50}$ (µm) | Z-pot. |
|---|---|---|---|---|---|
| — | 5.88E+07 | 1.35 | 4.65 | 4.22 | 46.9 |
| 135 | 8.27E+08 | 1.23 | 3.70 | 2.35 | 20.3 |
| 270 | 8.61E+08 | 1.39 | 4.12 | 3.35 | −4.3 |
| 540 | 1.04E+09 | 1.31 | 3.85 | 3.34 | −6.3 |

Preparations with increasing amounts of anionic micelles, result in increasing amounts of microbubble. Furthermore, surface charge properties can be also modulated (zeta potential values varying from positive to negative) as desired.

Example 26

Preparation of Assemblies from Gas Emulsion

Negatively charged microbubbles are obtained according to Example 24a using $C_4F_{10}$ as gas phase and DPPS as phospholipid (2 mg/ml) to stabilized microbubbles. After bubble generation by high speed mechanical emulsification (Megatron® MT3000, Kinematica, Switzerland) of the DPPS liposome suspension, the microbubbles are washed by diafiltration for 30 minutes using a 1 μm polycarbonate membrane (Nuclepore®), to remove the excess of phospholipids in the bubble suspension. Cationic micelles containing DPEPC and DSPE-PEG2000 conjugated to rat antimouse monoclonal IgG1 against P-selectin (70:30 in molar ratio, 5 mg/ml) are added to the bubble suspension (50 μl of micelles for 1 ml of microbubbles about $5 \times 10^9$ bubbles/ml). The mixture is gently stirred for 30 min at room temperature and centrifuged. The assemblies (supernatant) are resuspended in a 10% maltose solution, frozen and lyophilised (2 ml/vial). After freeze-drying, lyophilisates are gassed with $C_4F_{10}$ and reconstituted with 2 ml distilled water. The Coulter analysis showed that more than 90% of bubble-micelles assemblies were still intact after lyophilisation. These microbubbles showed a $D_N$ of 1.3 μm and $D_V$ of 2.9 μm. Flow cytometry measurements confirmed the presence of the biochemically active IgG1 antibody at the surface of the assemblies.

The invention claimed is:

1. An assembly comprising
a gas-filled microvesicle bearing a first overall net charge and
a component associated with said microvesicle wherein said component is a micelle, which bears a second overall net charge opposite in sign to said first net charge, consisting of
one or more amphiphilic compounds; and
a targeting ligand, bioactive agent, or a combination thereof,
and wherein said associated component has a diameter of 100 nm or lower, and is substantially free of magnetic particles.

2. An assembly according to claim 1 wherein said associated component has a diameter of 80 nm or lower.

3. An assembly according to claim 1 wherein said associated component has a diameter of 50 nm or lower.

4. An assembly according to claim 1 wherein said one or more amphiphilic compounds is selected from the group consisting of ($C_2$-$C_{10}$) organic acids, organic fatty acids comprising a ($C_{12}$-$C_{24}$) aliphatic chain, pharmaceutically acceptable salts thereof, esters thereof with polyoxyethylene; polyionic (alkali) salts; organic amines; amides; quaternary amine salts; amino acids; phospholipids; esters of mono- or oligo-saccharides with ($C_{12}$-$C_{24}$)organic fatty acids; organic sulfonates; perfluoroorganic acids; polymeric surfactants; and mixtures thereof.

5. An assembly according to claim 1 wherein the ratio between the number of charges per mole of microvesicles and the number of charges per mole of the associated component is from about 10:1 to about 1:10.

6. An assembly according to claim 5 wherein said ratio is of about 3:1 or less.

7. An assembly according to claim 5 wherein said ratio is of about 2:1 or less.

8. An assembly according to claim 1 wherein said microvesicle is a microbubble stabilized by an envelope comprising an amphiphilic film-forming compound or a microballoon having a material envelope.

9. An assembly according to claim 8 wherein said amphiphilic film-forming compound is a phospholipid.

10. An assembly according to claim 8 wherein said envelope or material envelope comprises a phospholipid or a lipid bearing a positive or negative net charge.

11. An assembly according to claim 10 wherein said phospholipid or lipid is selected fioni the group consisting of phosphatidylserine derivatives, phosphatic ic acid derivatives, phosphatidylglycerol derivatives, polyethyleneglycol modified phosphatidylethanolamines, ethylphosphatidylcholine derivatives and the respective lyso-forms; cholic acid salts; deoxycholic acid salts; glycocholic acid salts; ($C_{12}$-$C_{24}$) fatty acid salts thereof; alkylainmonium salts comprising at least one ($C_{10}$-$C_{20}$) alkyl chain; tertiary or quaternary ammonium salts comprising at least one ($C_{10}$-$C_{20}$) acyl chain linked to the nitrogen atom through a ($C_3$-$C_6$) alkylene bridge; and mixtures thereof.

12. An assembly according to claim 8 wherein the material envelope of said microballoon comprises a polymeric material, a proteinaceous material, a water insoluble lipid or any combination thereof.

13. An assembly according to claim 8 wherein the material envelope of said microballoon comprises an ionic biodegradable polymer.

14. An assembly accordine to claim 1 wherein said one or more amphiphilic compounds is selected from the group consisting of a polyethyleneglycol modified phospholipid; an alkylammonium salt comprising at least one ($C_{10}$-$C_{20}$) alkyl chain; a tertiary or quaternary ammonium salt comprising at least one ($C_{10}$-$C_{20}$) acyl chain linked to the nitrogen atom through a ($C_3$-$C_6$) alkylene bridge; a ($C_{12}$-$C_{24}$) fatty acid salt; a polymeric surfactant; and mixtures thereof.

15. An assembly according to claim 1 wherein said one or more amphiphilic compounds is selected from the group consisting of ($C_{12}$-$C_{24}$) fatty acid di-esters of phosphatidylcholine, ethylphosphatidylcholine, phosphatidylglycerol, phosphatidic acid, phosphaddyethanolamine, phosphatidylserine, sphingomyelin, and mixtures thereof.

16. An assembly according to claim 1 wherein said one or more amphiphilic compounds is selected from the group consisting of a phospholipid, a lipid hearing a positive or negative net charge, a polymeric ionic surfactant, and mixtures thereof.

17. An assembly according to claim 16 wherein said one or more amphiphilic compounds is selected from the group consisting of phosphatidylserine derivatives, phosphatidic acid derivatives, phosphatidylglycerol derivatives, polyethyleneglycol modified phosphatidylethanolamines, ethylphosphatidylcholine derivatives and the respective lyso-forms; cholic acid salts; deoxycholic acid salts; glycocholic acid salts; ($C_{12}$-$C_{24}$) fatty acid salts thereof; alkylammonium salts comprising at least one ($C_{10}$-$C_{20}$) alkyl chain; tertiary or quaternary ammonium salts comprising at least one ($C_{10}$-$C_{20}$) acyl chain linked to the nitrogen atom through a ($C_3$-$C_6$) all bridge; and mixtures thereof.

18. An aqueous suspension of a physiologically acceptable liquid comprising an assembly according to claim 1.

19. An assembly according to claim 1, wherein an aqueous suspension of said assembly in a pharmaceutically acceptable carrier shows a ζ-potential which is decreased of at least 50% in absolute value with respect to the ζ-potential of an aqueous suspension in the same carrier of the gas-filled microvesicles forming said assembly.

20. An assembly according to claim 19 wherein said ζ-potential is decreased of at least 75% in absolute value.

21. An assembly according to claim 19 wherein said ζ-potential is decreased of about 100% or more in absolute value.

22. A method for preparing an assembly according to claim 1, which comprises admixing a preparation comprising gas-filled microvesicles or a precursor thereof with a preparation comprising a component or a precursor thereof to be associated to said microvesicles.

23. A method according to claim 22 which comprises:
1) preparing a first aqueous suspension comprising a gas-filled microvesicle;
2) preparing a second aqueous suspension comprising a component to be associated with said gas-filled microvesicle;
3) admixing said two suspensions, to obtain an aqueous suspension comprising said assembly.

24. A method according to claim 22 which comprises:
1) preparing a first aqueous suspension comprising a gas-filled microvesicle;
2) freeze-drying said first suspension, to obtain a first lyophilized product;
3) preparing a second suspension comprising a component to be associated with said gas-filled microvesicle;
4) freeze-drying said, second suspension, to obtain a second, lyophilized product;
5) reconstituting said first and said second lyophilized product with a physiologically acceptable aqueous carrier in the presence of a gas, to obtain an aqueous suspension comprising the assembly.

25. A method according io claim 24, wherein step 5) comprises the steps of:
a) reconstituting the second lyophilized product with a physiologically acceptable aqueous carrier to obtain a suspension comprising the component to he associated to the gas-filled microvesicle; and
b) reconstituting the first lyophilized product with said suspension in the presence of a gas.

26. A method according to claim 22 which comprises:
1) preparing an aqueous emulsion comprisina an organic solvent, a nhospholipid and a lyoprotecting agent;
2) preparing an aqueous suspension comprising a component to be associated vith a gas-filled microvesicle;
3) admixing said aqueous suspension with said aqueous emulsion; and
4freeze drying the mixture to remove the water and the organic solvent, to obtain a lyophilized product comprising said assembly.

27. A pharmaceutically active formulation comprising an assembly according to claim 1.

28. A method for ultrasound diagnostic imaging which comprises administering a contrast-enhancing amount of an aqueous suspension of an assembly according to claim 1.

29. A method of therapeutic treatment which comprises administering a therapeutically-effective amount of an aqueous suspension of an assembly comprising a bioactive agent as defined in claim 1.

30. The assembly according claim 1, wherein said component associated with said microvesicle has a mean dimension which is at least 10 times smaller than the mean dimension of said microvesicle.

31. The assembly according to claim 1, wherein said component associated with said microvesicle has a mean dimension which is from 10 to 1000 times smaller than the mean dimension of said microvesicle.

32. The assembly according to claim 1, wherein the mean diameter in number of said assembly is not higher than about 30% the mean diameter of said microvesicle.

* * * * *

UNITED STATES PATENT AND TRADEMARK OFFICE
CERTIFICATE OF CORRECTION

PATENT NO. : 9,750,821 B2
APPLICATION NO. : 10/584327
DATED : September 5, 2017
INVENTOR(S) : Michel Schneider et al.

Page 1 of 1

It is certified that error appears in the above-identified patent and that said Letters Patent is hereby corrected as shown below:

In the Claims

Column 52, Claim 11, Line 2 replace "selected fioni the group consisting of" with --selected from the group consisting of--; Line 3 replace "phosphatic ic acid" with --phosphatidic acid--; Line 8 replace "alkylainmonium" with --alkylammonium--;

Column 52, Claim 15, Line 33 replace "phosphaddylethanolamine" with --phosphatidylethanolamine--;

Column 52, Claim 16, Line 37 replace "a lipid hearing" with --a lipid bearing--; and Column 52, Claim 17, Line 51 replace "all bridge" with --alkylene bridge--.

Signed and Sealed this
Ninth Day of January, 2018

Joseph Matal
*Performing the Functions and Duties of the
Under Secretary of Commerce for Intellectual Property and
Director of the United States Patent and Trademark Office*